United States Patent
Kalinichenko et al.

(10) Patent No.: US 11,026,933 B2
(45) Date of Patent: *Jun. 8, 2021

(54) COMPOSITIONS AND METHODS FOR TREATMENT OF CANCER

(71) Applicant: Children's Hospital Medical Center, Cincinnati, OH (US)

(72) Inventors: Vladimir Kalinichenko, Cincinnati, OH (US); Tatiana Kalin, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 257 days.

This patent is subject to a terminal disclaimer.

(21) Appl. No.: 16/332,404

(22) PCT Filed: Sep. 20, 2017

(86) PCT No.: PCT/US2017/052378
§ 371 (c)(1),
(2) Date: Mar. 12, 2019

(87) PCT Pub. No.: WO2018/057550
PCT Pub. Date: Mar. 29, 2018

(65) Prior Publication Data
US 2021/0023066 A1    Jan. 28, 2021

Related U.S. Application Data

(60) Provisional application No. 62/396,992, filed on Sep. 20, 2016.

(51) Int. Cl.
*A61K 31/4436* (2006.01)
*A61P 31/00* (2006.01)
*A61K 45/06* (2006.01)

(52) U.S. Cl.
CPC .......... *A61K 31/4436* (2013.01); *A61K 45/06* (2013.01); *A61P 31/00* (2018.01)

(58) Field of Classification Search
None
See application file for complete search history.

(56) References Cited

U.S. PATENT DOCUMENTS

| | | |
|---|---|---|
| 2006/0014686 A1 | 1/2006 | Wonsey et al. |
| 2007/0015799 A1 | 1/2007 | Ashton et al. |
| 2011/0257146 A1 | 10/2011 | Li et al. |
| 2017/0105982 A1 | 4/2017 | Kalinichenko et al. |

FOREIGN PATENT DOCUMENTS

WO    WO 2011/127297 A1    10/2011

OTHER PUBLICATIONS

Balli, D., et al., "Foxm1 transcription factor is required for lung fibrosis and epithelial-to-mesenchymal transition," EMBO J, 2013, 32:23144, 14 pgs.
Balli, D., et al., "Endothelial Cell-specific Deletion of Transcription Factor FOXM1 Increases Urethane-induced Lung Carcinogenesis," Cancer Res, 2011, 71:40-50, 19 pgs.
Behren, A., et al., "Phenotype-assisted transcriptome analysis identifies FOXM1 downstream from Ras-MKK3-p38 to regulate in vitro cellular invasion," Oncogene, 2010, 29:1519-30, 12 pgs.
Bhat, U.G., et al., "Thiazole Antibiotics Target FoxM1 and Induce Apoptosis in Human Cancer Cells," PLoS ONE, 2009, 4:e5592, 7 pgs.
Butcher, L., "Solid Tumors: Prevalence, Economics, and Implications for Payers and Purchasers," Biotechnology Healthcare, 2008, 5(1):20-21, 2 pgs.
Cai, Y., et al., "Foxm1 Expression in Prostate Epithelial Cells is Essential for Prostate Carcinogenesis," J Biol Chem, 2013, 288(31):22527-41, 15 pgs.
Carter, S.L., et al., "A signature of chromosomal instability inferred from gene expression profiles predicts clinical outcome in multiple human cancers," Nat Genet, 2006, 38(9):1043-8, 6 pgs.
Cheng, X.H., et al., "SPDEF Inhibits Prostate Carcinogenesis by Disrupting a Positive Feedback Loop in Regulation of the Foxm1 Oncogene," PLoS Genet, 2014, 10(9):e1004656, 14 pgs.
Compound Summary for CID 4273985, ST045931, PubChem Open Chemistry Databse, deposited on Sep. 14, 2005, 8 pgs.
Costa, R.H., et al., "New and unexpected: forkhead meets ARF," Curr Opin Genet Dev, 2005, 15:42-48, 7 pgs.
Gemenetzidis, E., et al., "FOXM1 Upregulation is an Early Event in Human Squamous Cell Carcinoma and it is Enhanced by Nicotine during Malignant Transformation," PloS One, 2009, 4(3):e4849, 18 pgs.
Gormally, M. V., et al., "Suppression of the FOXM1 trascriptional program via novel small molecule inhibition," Nat Commun, 2014, 5:5165 [Epub ahead of print], 25 pgs.
Gusarova, G.A., et al., "A cell-penetrating ARF peptide inhibitor of FoxM1 in mouse hepatocellular carcinoma treatment," J Clin Invest, 2007, 117(1):99-111, 13 pgs.
Halasi, M. et al., "Targeting FOXM1 in cancer," Biochem Pharmacol, 2013, 85:644-652, 9 pgs.
Kalin, T. V., et al., "Increased Levels of the FoxM1 Transcription Factor Accelerate Development and Progression of Prostate Carcinomas in both TRAMP and LADY Transgenic Mice," Cancer Res, 2006, 66:1712-1720, 9 pgs.
Kalin, T. V., et al., "Multiple faces of FoxM1 transcription factor: Lessons from transgenic mouse models," Cell Cycle, 2011, 10(3):396-405, 10 pgs.

(Continued)

*Primary Examiner* — Thomas S Heard
(74) *Attorney, Agent, or Firm* — Frost Brown Todd LLC; Nicole M. Tepe

(57) ABSTRACT

Disclosed are methods and compositions for the treatment of a proliferative disorder characterized by increased expression of the FOXM1 gene. Exemplary disorders include adenocarcinoma, melanoma, rhabdomyosarcoma, non-small cell lung cancer (NSCLC), head and neck squamous carcinoma, hepatocellular carcinoma (HCC), intrahepatic cholangiocarcinoma, colon carcinoma, basal cell carcinoma, infiltrating ductal breast carcinoma, anaplastic astrocytoma, glioblastoma, pancreatic carcinoma, gastric cancer, acute myeloid leukemia, lung cancer, liver cancer, breast cancer, prostate cancer, a brain cancer. Kits and articles of manufacture comprising compositions for such treatment are also disclosed.

11 Claims, 11 Drawing Sheets

(56) References Cited

OTHER PUBLICATIONS

Kalininchenko, V. V., et al., "Developing FOXM1 Inhibitors to Suppress Goblet Cell Metaplasia and Airways Hyperresonsiveness," Am J Resp Crit Care Med, 2016, 193:A6484, 3 pgs.

Kalinichenko, V. V., et al., "Forkm1b transcription factor is essential for development of hepatocellular carcinomas and is negatively regulated by the p19$^{ARF}$ tumor suppressor," Genes & Development, 2004, 18:830-850, 21 pgs.

Kim, I-M et al., "The Forkhead Box m1 Transcription Factor Stimulates the Proliferation of Tumor Cells during Development of Lung Cancer," Cancer Res, 2006, 66(4):2153-2161, 9 pgs.

Korver, W., et al., "The winged-helix transcription factor Trident is expressed in cycling cells" Nucleic Acids Res, 1997, 25(9):1715-1719, 5 pgs.

Lee, J.S., et al., "Classification and Prediction of Survival in Hepatocellular Carcinoma by Gene Expression Profiling," Hepatology, 2004, 40:667-676, 10 pgs.

Li, Q., et al., "Critical Role and Regulation of Transcription Factor FoxM1 in Human Gastric Cancer Angiogenesis and Progression," Cancer Research, 2009, 69(8):3501-3509, 22 pgs.

McCormick, F., "Signalling networks that cause cancer," Trends Cell Biol, 1999, 9:M53-M56, 4 pgs.

McGovern, U.B., et al., "Gefitinib (Iressa) represses FOXM1 expression via FOXO3a in breast cancer," Mol Cancer Ther, 2009, 8(3):582-91, 10 pgs.

Miannay, B., et al., "Logic programming reveals alteration of key transcription factors in multiple myeloma," Sci Rep, 2017, 7:9257, 12 pgs.

Milewski, D., et al., "FoxF1 and FoxF2 transcription factors synergistically promote rhabdomyosarcoma carcinogenesis by repressing transcription of p21$^{Cip1}$ CDK inhibitor," Oncogene, 2017, 36(6):850-862, 31 pgs.

Myatt, S.S., et al., "The emerging roles of forkhead box (Fox) proteins in cancer," Nature Reviews, 2007, 7:847-859, 13 pgs.

Nakamura, S., et al., "The FOXM1 transcriptional factor promotes the proliferation of leukemia cells through modulation of cell cycle progression in acute myeloid leukemia," Carcinogenesis, 2010, 31(11):2012-2021, 10 pgs.

Pilarsky, C. et al., "Identification and Validation of Commonly Overexpressed Genes in Solid Tumors by Comparison of Microarray Data," Neoplasia, 2004, 6:(6)744-750, 7 pgs.

Ren, X., et al., "FOXM1 Promotes Allergen-Induced Goblet Cell Metaplasia and Pulmonary Inflammation," Mol Cell Biol, 2013, 33(2):371-86, 16 pgs.

Sherr, C.J., et al., "The RB and p53 pathways in cancer," Cancer Cell, 2002, 2:103-112, 10 pgs.

Sun, L., et al., "The FOXM1 inhibitor RCM-1 suppresses goblet cell metaplasia and prevents IL-13 and STAT6 signaling in allergen-exposed mice," Sci Signal, 2017, 10:Eaai8583, 10 pgs.

Teh, M-T., et al., "FOXM1 is a Downstream Target of Gli1 in Basal Cell Carcinomas," Cancer Research, 2002, 62:4773-4780, 8 pgs.

Troy, D.B. (ed.), Remington: The Science and Practice of Pharmacy, 21$^{st}$ Ed, Lippincott Williams & Wilkins, Philadelphia, PA, 2006, 6 pgs. (Table of Contents Only).

Wang, I.C., et al., "Forkhead Box M1 Regulates the Transcriptional Network of Genes Essential for Mitotic Progression and Genes Encoding the SCF (Skp2-Cks1) Ubiquitin Ligase," Mol Cell Biol, 2005, 25(24):10875-10894, 20 pgs.

Wang, I.C., et al., "FoxM1 Regulates Transcription of JNK1 to promote the $G_1$/S Transition and Tumor Cell Invasiveness," J Biol Chem, 2008a, 283(30):20770-8, 9 pgs.

Wang, I.C., et al., "Transgenic expression of the forkhead box M1 transcription factor induces formation of lung tumors," Oncogene, 2008b, 27:4137-4149, 13 pgs.

Wang, I.C., et al., "Foxm1 transcription factor is required for the intiation of lung tumorigenesis by oncogenic Kras$^{G12D}$," Oncogene, 2014, 33:2591-5396, 6 pgs.

Ye, H., et al., "Hepatocyte Nuclear Factor 3/fork head Homolog 11 is Expressed in Proliferating Epithelial and Mesenchymal Cells of Embryonic and Adult Tissues," Mol Cell Biol, 1997, 17(3):1626-1641, 16 ps.

Yoshida, Y., et al., "The Forkhead Box M1 Transcription Factor Contributes to the Development and Growth of Mouse Colorectal Cancer," Gastroenterology, 2007, 132:1420-1431, 12 pgs.

Zhang, N., et al., "FoxM1 Promotes β-catenin Nuclear Localization and Controls Wnt Target-Gene Expression and Glioma Tumorigenesis," Cancer Cell, 2011, 20(4):427-42, 27 pgs.

International Search Report and Written Opinion dated Nov. 14, 2017 for Application No. PCT/US2017/052378, 18 pgs.

U.S. Appl. No. 62/393,992, filed Sep. 20, 2016.

Chemical Block Ltd., Accession No. 339163-65-4, Jun. 1, 2001, Chemical Abstracts Service, Columbus, Ohio, downloaded Apr. 15, 2020, 2 pgs.

KOO, C-Y, et al., "FOXM1: From cancer initiation to progression and treatment," Biochimica et Biophysica Acta, 2012, 1819:28-37, 10 pgs.

PubChem, Compound Summary, 2-(2-Oxo-2(2-thienyl)ethylthio)-4,6-di(2-thienyl)pyridine-3-carbonitrile, dated Sep. 14, 2005 downloaded Apr. 14, 2020 from https://pubchem.nchi.nlm.nih.gov/compound/4273985, 14 pgs.

Shukla, S., et al., "The FOXM1 Inhibitor RCM-1 Decreases Carcinogenesis and Nuclear β-Catenin," Mol Cancer Ther, 2019, 18:1217-1229, 13 pgs.

Wang, Z., et al., "Forkhead box M1 transcription factor: A novel target for cancer therapy," Cancer Treatment Reviews, 2010, 36:151-156, 6 pgs.

European Search Report, Supplementary, and Written Opinion dated May 26, 2020 for Application No. EP 17853767.6, 15 pgs.

A. Effect on colony initiation (Treatment removed after 3 days)

B. Effect on colony progression (Treatment added after 3 days)

COMPOSITIONS AND METHODS FOR TREATMENT OF CANCER

CROSS-REFERENCE TO RELATED APPLICATIONS

This application claims priority to and benefit of International Application No. PCT/US2017/052378, filed Sep. 20, 2017, entitled "Compositions and Methods for Treatment of Cancer," which claims the benefit of and priority to U.S. Provisional Application No. 62/396,992, filed Sep. 20, 2016.

BACKGROUND

It is estimated that by 2020, 18.2 million Americans, roughly 1 in 19 people, will be cancer patients or survivors, up from 11.7 million (1 in 26) in 2005. The overall cost of cancer in America was $206 billion in 2006, according to the National Institutes of Health, including $78 billion for direct medical costs, $18 billion for lost productivity attributed to illness, and $110 billion for lost productivity. While, according to reports dated 2008, about half of the biologics in development were for cancer, more than four times the number for infectious diseases or autoimmune disorders, the need for treatment of cancers, particularly those associated with the presence of solid tumors, remains significant. Butcher L. Solid Tumors: Prevalence, Economics, And Implications for Payers and Purchasers. *Biotechnology healthcare.* 2008; 5(1):20-21. Cancers such as human non-small cell lung cancers (NSCLC), head and neck squamous carcinomas, hepatocellular carcinomas (HCC), intrahepatic cholangiocarcinomas, colon carcinomas, basal cell carcinomas, breast cancer, including infiltrating ductal breast carcinomas, anaplastic astrocytomas, glioblastomas, pancreatic carcinomas, gastric cancer, acute myeloid leukemia, prostate adenocarcinoma, lung adenocarcinoma, glioblastomas, colorectal cancer, gastric cancer, hepatic cancer, lung cancer, ovarian cancer, neuroblastoma, and multiple myeloma are all cancers which contribute to the large incidence of cancer in the population, in the US and outside the US. There remains a need in the art for compositions and methods of treating such cancers. The instant disclosure addresses one or more of the aforementioned needs in the art.

BRIEF SUMMARY

Disclosed are methods and compositions for the treatment of a proliferative disorder characterized by increased expression of the FOXM1 gene. Exemplary disorders include adenocarcinoma, melanoma, rhabdomyosarcoma, non-small cell lung cancer (NSCLC), head and neck squamous carcinoma, hepatocellular carcinoma (HCC), intrahepatic cholangiocarcinoma, colon carcinoma, basal cell carcinoma, infiltrating ductal breast carcinoma, anaplastic astrocytoma, glioblastoma, pancreatic carcinoma, gastric cancer, acute myeloid leukemia, lung cancer, liver cancer, breast cancer, prostate cancer, a brain cancer. Kits and articles of manufacture comprising compositions for such treatment are also disclosed.

DETAILED DESCRIPTION OF THE INVENTION

Definitions

Figure 1:
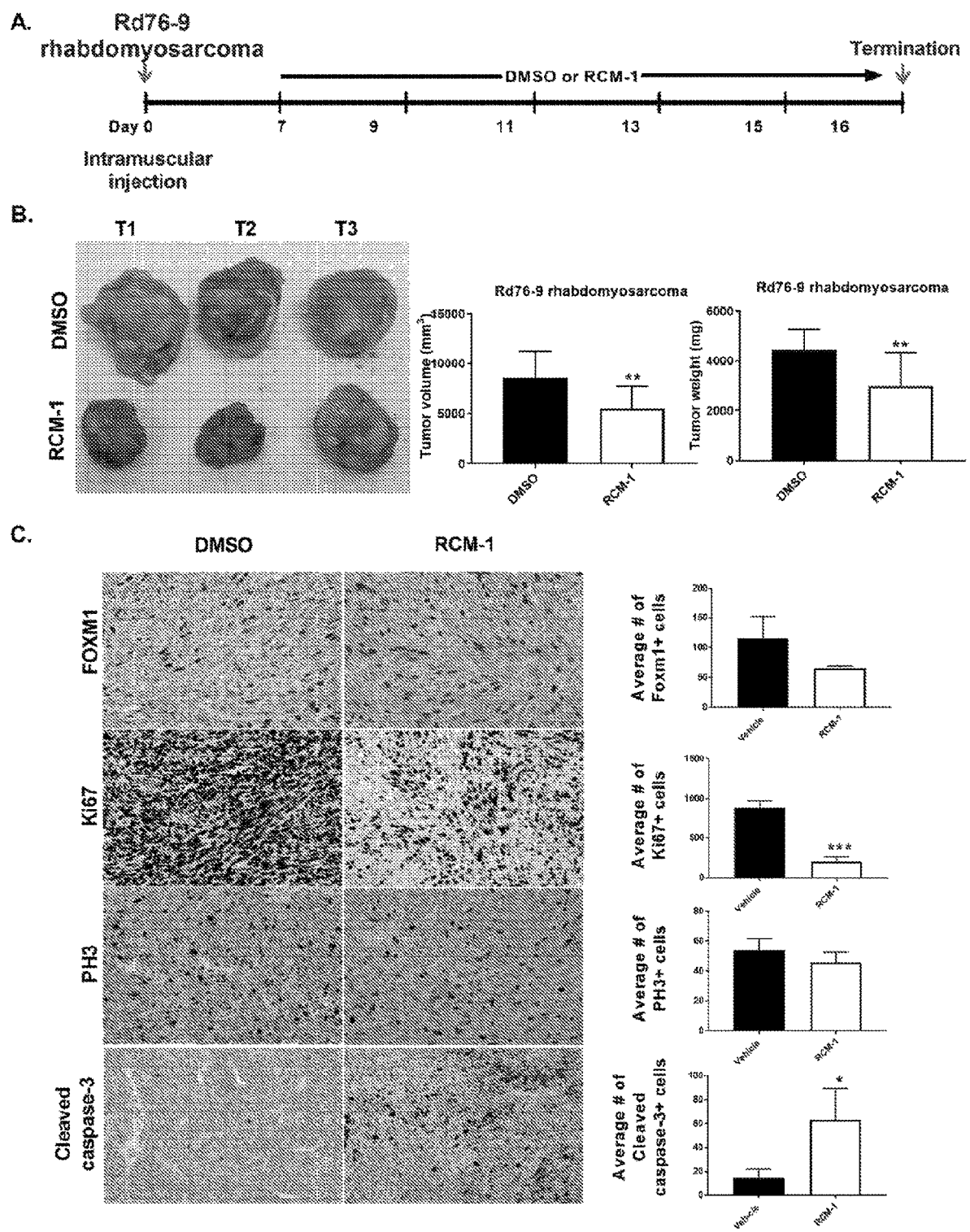
FIG. 1. RCM-1 treatment reduces growth of Rd76-9 rhabdomyosarcomas in mice. (A) Schematic representation of the experimental protocol. Mouse Rd76-9 rhabdomyosarcoma cells (1×106 cells) were injected intramuscularly in the flanks of C56B1/6J mice (n=8 mice per group). Seven days after the tumor cells inoculation, 40 µL of either Vehicle (DMSO) or RCM1 (20 mg/Kg body weight) were injected intraperitoneally in the animals every other day. The animals were sacrificed and tumors were harvested on day 16. (B) RCM-1 treatment decreased Rd76-9 tumor growth as compared to the DMSO-treated group. The photographs show the differences in the tumor sizes between DMSO- or RCM-1-treated Rd76-9 tumors. The graphs show the average tumor mass and tumor volume, and presented as mean±SD *$p<0.05$, $p<0.01$ and *$p<0.001$ compared to the DMSO-treated control group. (C) RCM-1 treatment decreased tumor cell proliferation and increased apoptosis in Rd76-9 rhabdomyosarcoma tumors. Paraffin-embedded sections of DMSO- or RCM-1-treated Rd76-9 tumors were stained with antibodies against FOXM1, Ki67, PH3 and Cleaved caspase-3 (magnification ×200). The RCM-1-treated Rd76-9 tumors showed reduced FOXM1 staining and decreased expression of proliferation-specific markers Ki67 and PH3. Cleaved caspase staining was increased in the RCM-1 treated tumors, indicating an increase in apoptosis. The graphs in the right panel show the average numbers of FOXM1, Ki67, PH3 and Cleaved caspase-3-positive cells in both groups. Positive cells were counted in 5 random microscopic fields per group and the numbers are presented as mean±SD. *$p<0.05$, $p<0.01$ and *$p<0.001$ compared to the DMSO-treated control group.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms refer to children.

"Therapeutically effective amount" relates to the amount or dose of an active compound or composition described herein that will lead to one or more therapeutic effect, in particular, a desired beneficial effects. A therapeutically effective amount of a substance can vary according to factors such as the disease state, age, sex, and weight of the subject, and the ability of the substance to elicit a desired response in the subject. Dosage regime may be adjusted to provide the optimum therapeutic response. For example, several divided doses may be administered daily or the dose may be proportionally reduced as indicated by the exigencies of the therapeutic situation.

The phrase "pharmaceutically acceptable," as used in connection with compositions of the disclosure, refers to molecular entities and other ingredients of such compositions that are physiologically tolerable and do not typically produce untoward reactions when administered to a subject (e.g., human) In certain embodiments, as used herein, the term "pharmaceutically acceptable" means approved by a regulatory agency of a Federal or a state government or listed in the U.S. Pharmacopeia or other generally recognized pharmacopeia for use in mammals (e.g., humans).

The terms "pharmaceutically acceptable salts" or "a pharmaceutically acceptable salt thereof" refer to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as The Merck Index. Any suitable constituent can be selected to make a salt of an active drug discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives of dextromethorphan and/or quinidine can also be suitable for use in the compositions and methods disclosed herein. In certain embodiments, the dextromethorphan is administered in the form of dextromethorphan hydrobromide, and the quinidine is administered in the form of quinidine sulfate. A salt of a compound of this disclosure may be formed between an acid and a basic group of the compound, such as an amino functional group, or a base and an acidic group of the compound, such as a carboxyl functional group. According to another embodiment, the compound is a pharmaceutically acceptable acid addition salt. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The term "carrier" applied to pharmaceutical compositions of the disclosure refers to a diluent, excipient, or vehicle with which an active compound (e.g., dextromethorphan) is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like. Suitable pharmaceutical carriers are described in "Remington's Pharmaceutical Sciences" (any edition).

The term "compound," as used herein, is also intended to include any salts, solvates, or hydrates thereof.

Disclosed herein are methods for the treatment of proliferative disorders in an individual in need thereof, particularly a cancer, more particularly, a cancer that overexpress the FOXM1 gene.

The FOXM1 protein (previously known as HFH-11B, Trident, Win, or MPP2) is a member of the Forkhead Box (FOX) family of transcription factors. FOXM1 is not expressed in adult normal tissues, but highly expressed in tumors, making FOXM1 an ideal target for cancer therapies (i.e., specific FOXM1 inhibitors will not affect the normal tissues). FOXM1 is upregulated in almost all cancers, and levels of FOXM1 correlate with metastasis and worst overall survival in cancer patients.

FOXM1 protein was extensively studied in various tumor cell lines and tumor tissues obtained from cancer patients. Microarray analysis of human solid tumors demonstrated that FOXM1 is one of the most common over-expressed gene in human tumors (1). FOXM1 was increased in human non-small cell lung cancers (NSCLC), head and neck squamous carcinomas, hepatocellular carcinomas (HCC), intra-hepatic cholangiocarcinomas, colon carcinomas, basal cell carcinomas, infiltrating ductal breast carcinomas, anaplastic astrocytomas, glioblastomas, pancreatic carcinomas, gastric cancer, acute myeloid leukemia and other human tumors and human neoplastic cell lines (2-10). Positive correlation was found between increased FOXM1 and poor prognosis in cancer patients. Studies with cultured human cancer lines and transgenic mice demonstrated that FOXM1 stimulates tumor cell proliferation, invasion and metastasis in many tumor types, including lung, liver, breast, prostate and brain cancers (reviewed in (11)).

FOXM1 expression is induced during cellular proliferation and is extinguished in terminally differentiated cells (Korver et al., 1997, Ye et al., 1997). FOXM1 is highly expressed in a variety of tissues during embryogenesis, and Foxm1$^{-/-}$ mice are embryonic lethal due to multiple abnormalities in the liver, heart, lung and blood vessels. FOXM1 is not expressed in adult tissues, but FOXM1 is re-activated during benign and malignant transformations and during organ injury and repair (Kahn et al., 2011). Elevated levels of FOXM1 correlated with high proliferation rates in human prostate adenocarcinomas (Kahn et al., 2006); (Cheng et al., 2014). In human lung adenocarcinomas, increased FOXM1 was correlated with higher grades of lung cancers and poor patient survival (Carter et al., 2006). Positive correlation was also found between FOXM1 overexpression and increased angiogenesis in human glioblastomas. In breast cancer patient samples, FOXM1 levels strongly associated with expression of estrogen receptor alpha. FOXM1 was overexpressed in HCC from patients that responded poorly to treatment. 4. Subgroup analysis showed that FOXM1 overexpression was associated with poor prognosis of colorectal cancer, gastric cancer, hepatic cancer, lung cancer and ovarian cancer. High expression level of FOXM1 was also associated with advanced tumor stage. High FOXM1 expression was associated with increased genomic instability and poor prognosis in cancer patients (Carter et al., 2006). FOXM1 regulates canonical Wnt signaling in neuroblastomas (Zhang et al., 2011). In multiple myeloma (MM) patients, FOXM1 is up-regulated (Miannay et al., 2017). The unique expression pattern of the transcription factor FOXM1 in the cancer tissue makes it an excellent cancer drug target in addition to its prognostic significance.

FOXM1 is a key downstream effector of the RAS/ERK signaling pathway (Wang et al., 2012, Behren et al., 2010, Wang et al., 2013). The RAS-ERK pathway induces cell cycle progression by activating the temporal expression of cyclin regulatory subunits that bind to and activate their corresponding cyclin-dependent kinases (CDK). CDK2/Cyclin E, CDK4/6/Cyclin D and CDK1/Cyclin B complexes phosphorylate and activate FOXM1 and a variety of other cell cycle regulatory proteins critical for G1/S and G2/M transitions (McCormick, 1999, Sherr and McCormick, 2002). In addition to CDK/Cyclin complexes, activated ERK1/2 and polo-like kinase 1 (PLK1) phosphorylate FOXM1, contributing to its transcriptional activation. FOXM1 binds to and induces transcription of cell cycle regulatory genes such as Cyclin B1, Cyclin A2, PLK1, JNK1, CDC25B, TOPO2 and Aurora B (Wang et al., 2005, Wang et al., 2008a, Wang et al., 2008b, Balli et al., 2011), and inhibits expression of p21Cip1 and p27Kip1 tumor suppressors. Inhibition of FOXM1 in cultured tumor cells with either siRNA or specific peptide inhibitor decreased DNA replication and delayed mitotic progression (McGovern et al., 2009, Bhat et al., 2009, Kalinichenko et al., 2004, Kahn et al., 2006).

To study the role of FOXM1 during carcinogenesis, various genetic mouse models have been generated (Kahn et al., 2006). Ubiquitous overexpression of FOXM1 in Rosa26-FoxM1 transgenic mice stimulated proliferation of lung tumor cells and increased the number and size of lung tumors induced by tobacco smoke derived carcinogen 3-methylcholanthrene (MCA) and promoted by butylated hydroxytoluene (BHT). Likewise, an increase in the number and size of colorectal tumors was found in Rosa26-FoxM1 mice treated with azoxymethane (AOM) and dextran sodium sulfate (DSS). FOXM1 cooperated with SV 40 T Antigen to accelerate initiation and progression of prostate adenocarcinomas in Rosa26-FoxM1/TRAMP and Rosa26-FoxM1/LADY double transgenic mice. Deletion of FOXM1 from all cell types in Mx-Cre/Foxm1fl/fl mice decreased urethane-mediated lung tumorigenesis and delayed the growth and progression of hepatocellular carcinoma (HCC) induced by DEN/phenobarbital treatment. Mice with hepatocyte-specific deletion of FOXM1 (Albumin-Cre Foxm1fl/fl) exhibited diminished proliferation of tumor cells and decreased formation of HCC after DEN/Phenobarbital induction. Likewise, reduced growth of colorectal tumors was found in Villin-Cre Foxm1fl/fl mice treated with AOM/DSS. Deletion of FOXM1 from respiratory epithelial cells (SPC-rtTA/tetO-Cre/Foxm1fl/fl transgenic mice) prior to the tumor initiation with urethane or MCA/BHT caused a striking reduction in the number and size of lung adenomas, whereas deletion of FOXM1 completely abrogated lung carcinogenesis induced by activated K-rasG12D (SPC-rtTA/tetO-Kras/tetO-Cre/Foxm1fl/fl mice) (Wang et al., 2013). Interestingly, a deletion of FOXM1 in preexisting lung tumors was sufficient to reduced tumor growth in the lung, indicating that FOXM1 is a promising target for antitumor therapy in cancer patients.

Discovery of protein-protein interactions between FOXM1 and the P19ARF tumor suppressor led to development of the ARF peptide, which specifically binds to the FOXM1 protein and sequesters it into nucleoli, thereby inhibiting FOXM1 transcriptional activity (Kalinichenko et al., 2004, Costa et al., 2005). Administration of ARF peptide to mice bearing hepatocellular carcinomas (HCC) inhibited HCC progression through specific binding and inactivation of the FOXM1 protein (Gusarova et al., 2007). Another recent study demonstrated that the ARF peptide was capable of inhibiting the FOXM1 protein in a mouse model of asthma (Ren et al., 2013). FOXM1-specific siRNA and shRNA were recently found to be effective in inhibiting FOXM1 protein in a mouse xenograft breast cancer model (reviewed in (Halasi and Gartel, 2013)). Thiazole antibiotics Siomycin A and thiostrepton inhibited FOXM1 in cultured tumor cells and in mouse tumor models (Halasi and Gartel, 2013). Both of these agents were found to be proteasome inhibitors and, therefore, stabilized the expression of multiple cellular proteins (Halasi and Gartel, 2013). A novel small molecule compound, FDI-6, has been described as a FOXM1 inhibitor that directly bound to FOXM1 protein and blocked FOXM1 binding to DNA. (Gormally et al., 2014).

Most recently, the RCM-1 compound was discovered by a high throughout screen of small molecule compounds. RCM-1 reduced FOXM1 nuclear localization, stimulated ubiquitination of FOXM1 and its translocation into proteasomes causing the degradation of the FOXM1 protein. While RCM-1 was very effective in inhibiting FOXM1 in animal models of asthma (Sun et al., 2017), its efficacy in tumor models was not tested.

Figure 4:
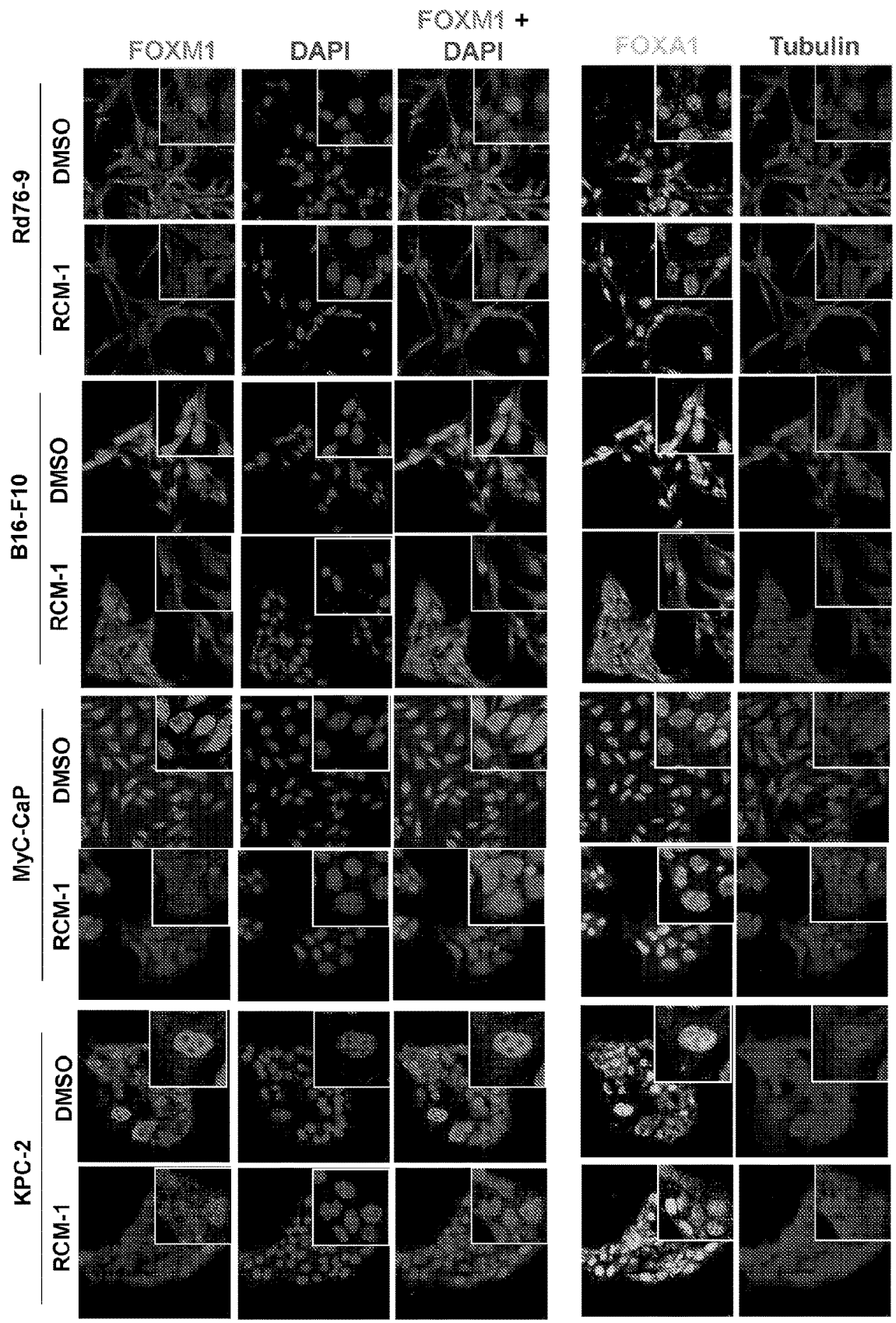
FIG. 4. RCM-1 decreased nuclear localization of FOXM1 in cancer cells. Rd76-9 rhabdomyosarcoma, B16-F10 melanoma, MyC-CaP prostate carcinoma, KPC-2 pancreatic carcinoma, A549 lung adenocarcinoma and 4T1 breast adenocarcinoma cell lines were treated with either DMSO or RCM-1 for 24 h in cell culture, and the cells were fixed and stained for FOXM1 (red), FOXA1 (green), and tubulin (cyan). DAPI (blue) was used to visualize cell nuclei. RCM-1 decreased nuclear localization of FOXM1, but did not affect FOXA1 localization, indicating the FOXM1 specific effect of RCM-1. The images are representative of 10 random microscopic fields in each treatment group (magnification ×400).
Figure 4:
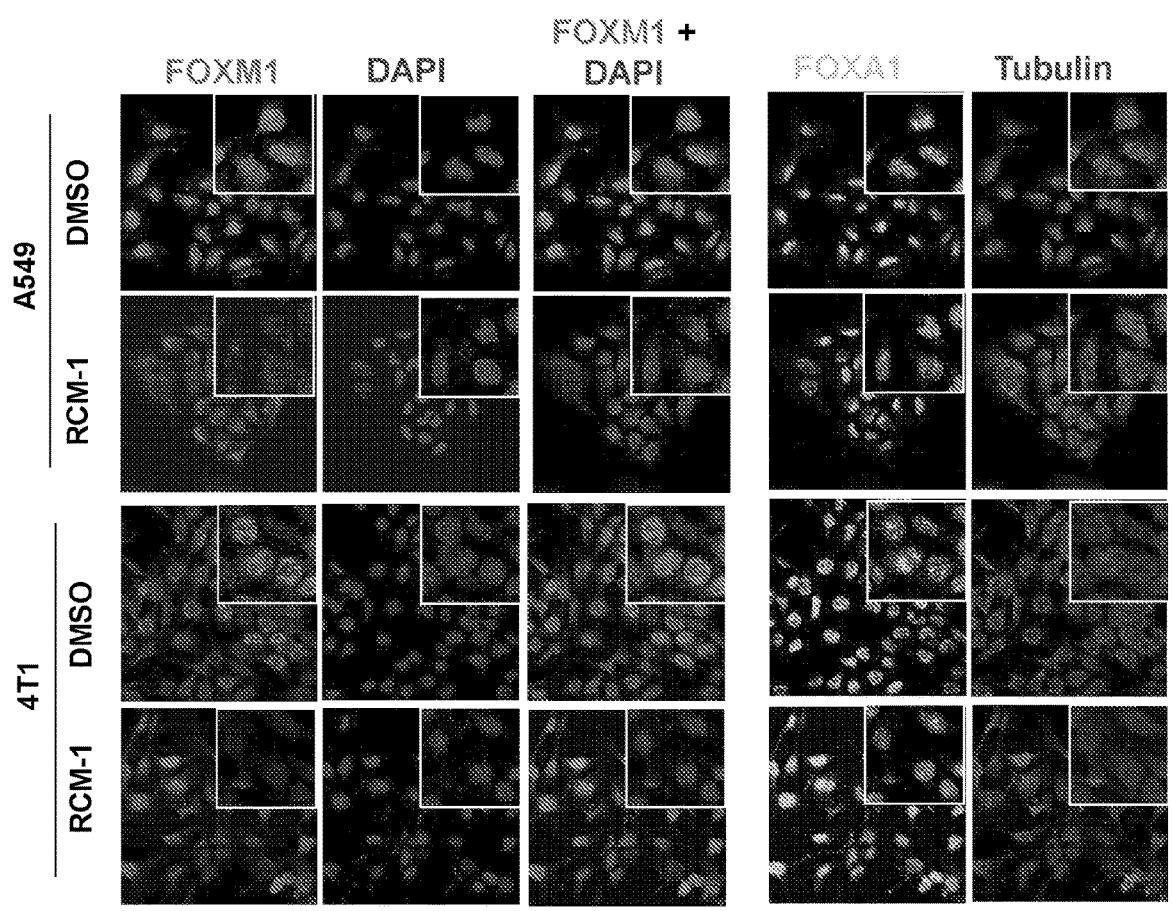
Figure 5:
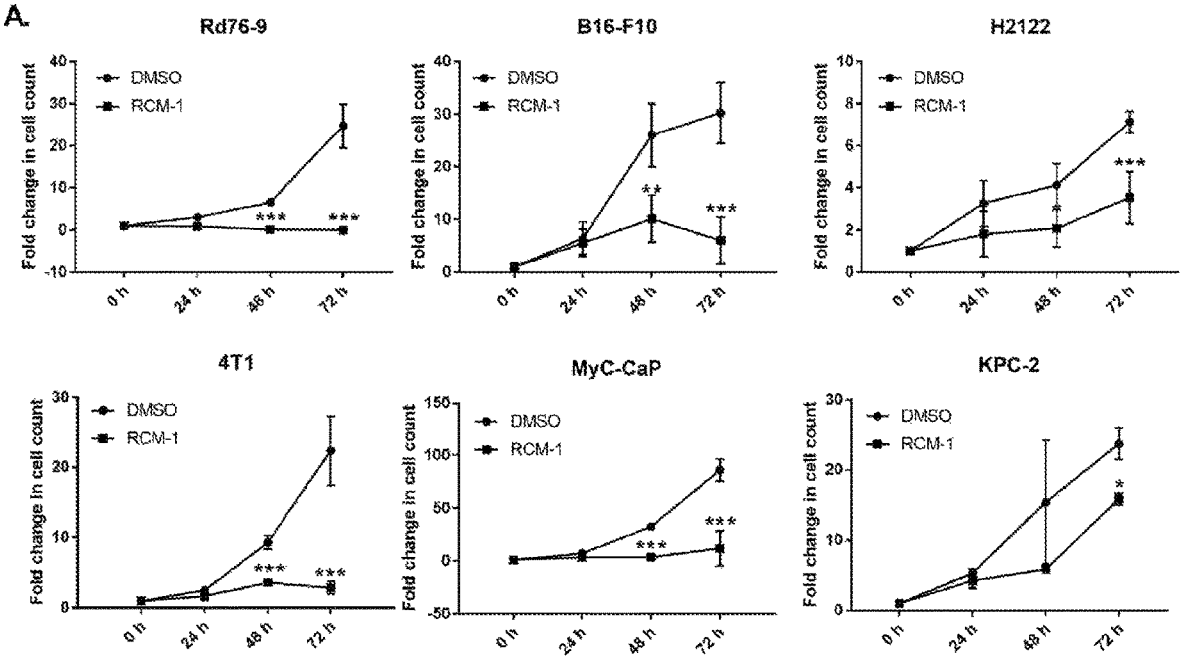
FIG. 5. RCM-1 inhibits cellular proliferation via increasing duration of cell cycle and mitosis in human and mouse cancer cell lines in vitro. (A) Rd76-9 rhabdomyosarcoma, B16-F10 melanoma, H2122 lung adenocarcinoma, 4T1 breast carcinoma, MyC-CaP prostate carcinoma and KPC-2 pancreatic carcinoma cells were seeded in 6-well plates and incubated overnight. The cells were treated with 20 μM concentration of RCM-1 for 24, 48 and 72 h and cell growth was analyzed by counting alive cells using trypan blue. Cells treated with DMSO were used as controls. The graphs represent the fold change in the cell count followed by RCM-1 treatment as compared to DMSO-treatment. The data were collected through three independent experiments and are presented as mean±SE. *p<0.05, p<0.01 and *p<0.001 compared to the DMSO-treatment. (B) Treatment with RCM-1 increased duration of mitosis and cell cycle in the cancer cell lines. Cells were grown in 24-well plates. Images were acquired on a motorized inverted epifluorescence microscope using phase-contrast live cell imaging. 4 fields per well were imaged every 5 min for 2 3 days. Mitotic duration was measured as the interval between nuclear envelope breakdown and anaphase onset. Cell cycle duration was measured as the interval between anaphase onset of the mother cell and its daughter cells. Values are shown as mean±SD. ns: p>0.05, p0.01, *p0.001 and ****p0.0001.
Figure 5:
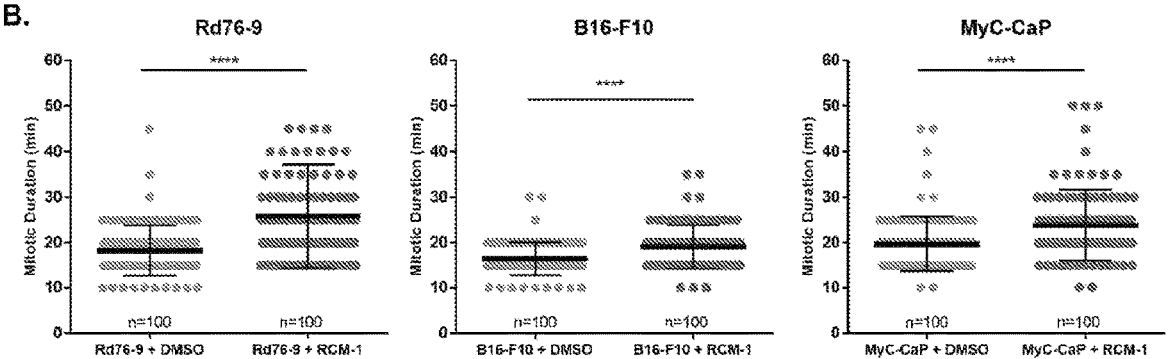
Figure 5:
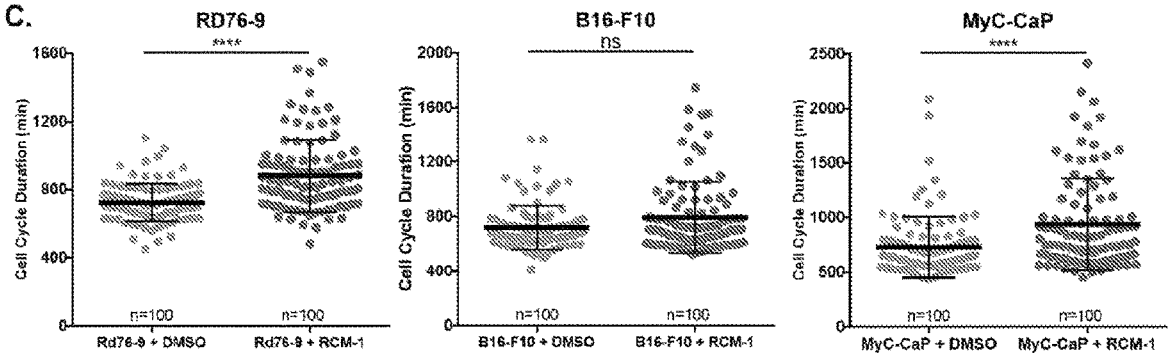
Figure 6:
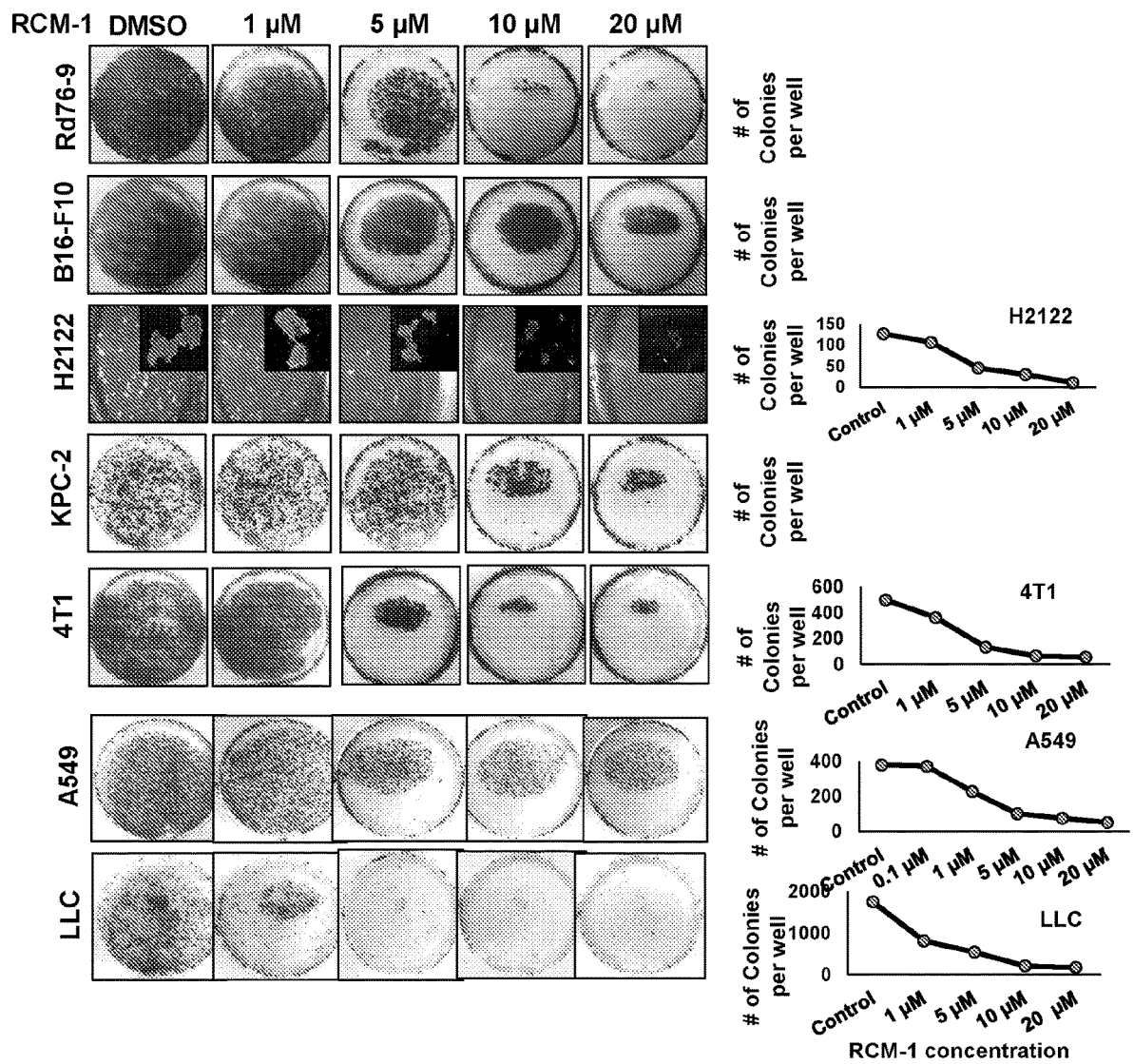
FIG. 6. RCM-1 inhibits colony formation of cancer cells in vitro in a dose-dependent manner Rhabdomyosarcoma Rd76-9, melanoma B16-F10, lung adenocarcinoma H2122, pancreatic ductal adenocarcinoma KPC-2, breast adenocarcinoma 4T1, lung adenocarcinoma A549 and LLC cells were seeded in 6-well plates and treated with 1 μM, 5 μM, 10 μM or 20 μM of RCM-1. DMSO-treated cells were used as controls. At day 7, the colonies were fixed and stained with 0.5% crystal violet and the number of DMSO- or RCM-1-treated colonies containing ≥50 cells were counted. The results were obtained from three independent experiments. The graphs represent the average number of tumor cell colonies per well in treatment groups.
Figure 7:
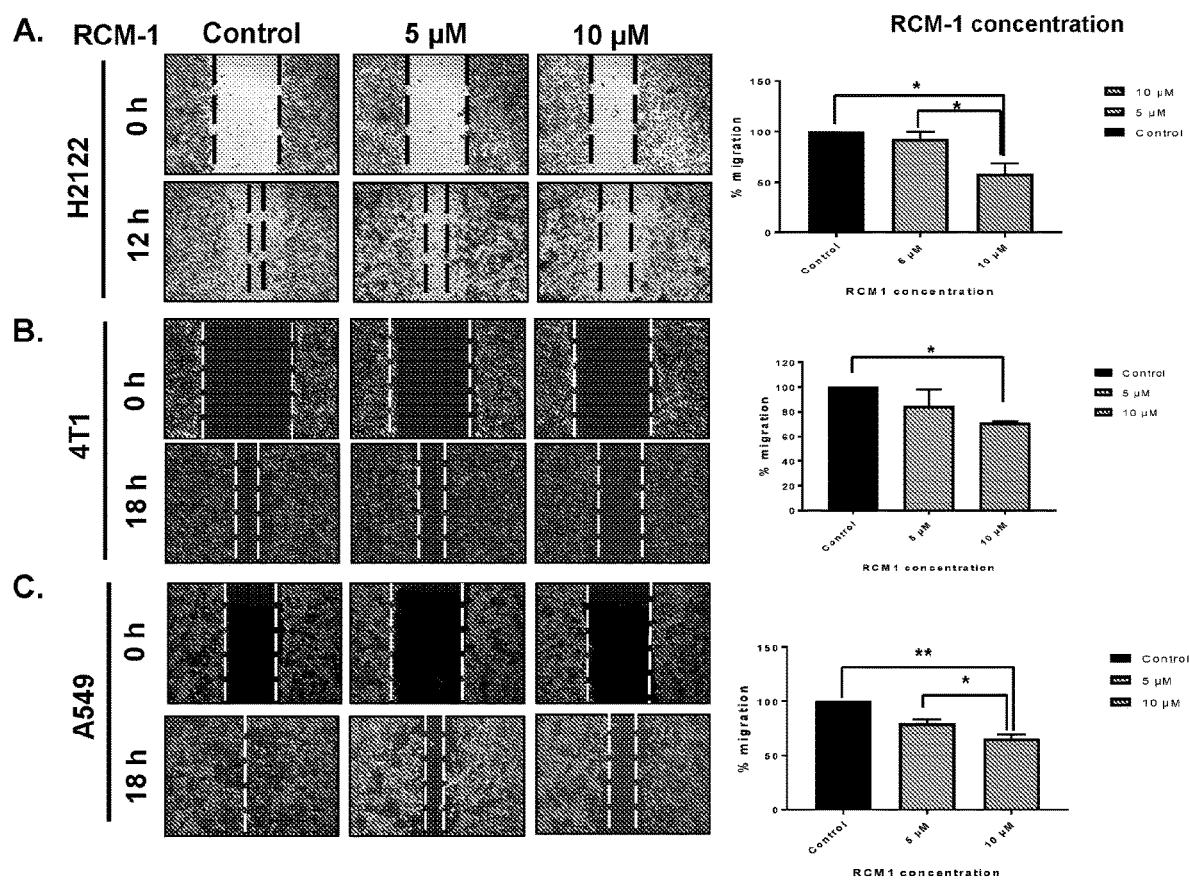
FIG. 7. RCM-1 inhibits migration of cancer cells in vitro in a dose-dependent manner Standardized scratches were created in subconfluent H2122, 4T1 and A549 cell cultures. Cells were treated with 5 μM or 10 μM of RCM-1 and cell migration was assessed after 12 h and 18 h. Data were presented as percent migration in RCM1-treated groups compared to DMSO-treatment (mean±SE). *p<0.05, p<0.01 and *p<0.001 compared to the DMSO-control.
Figure 8:
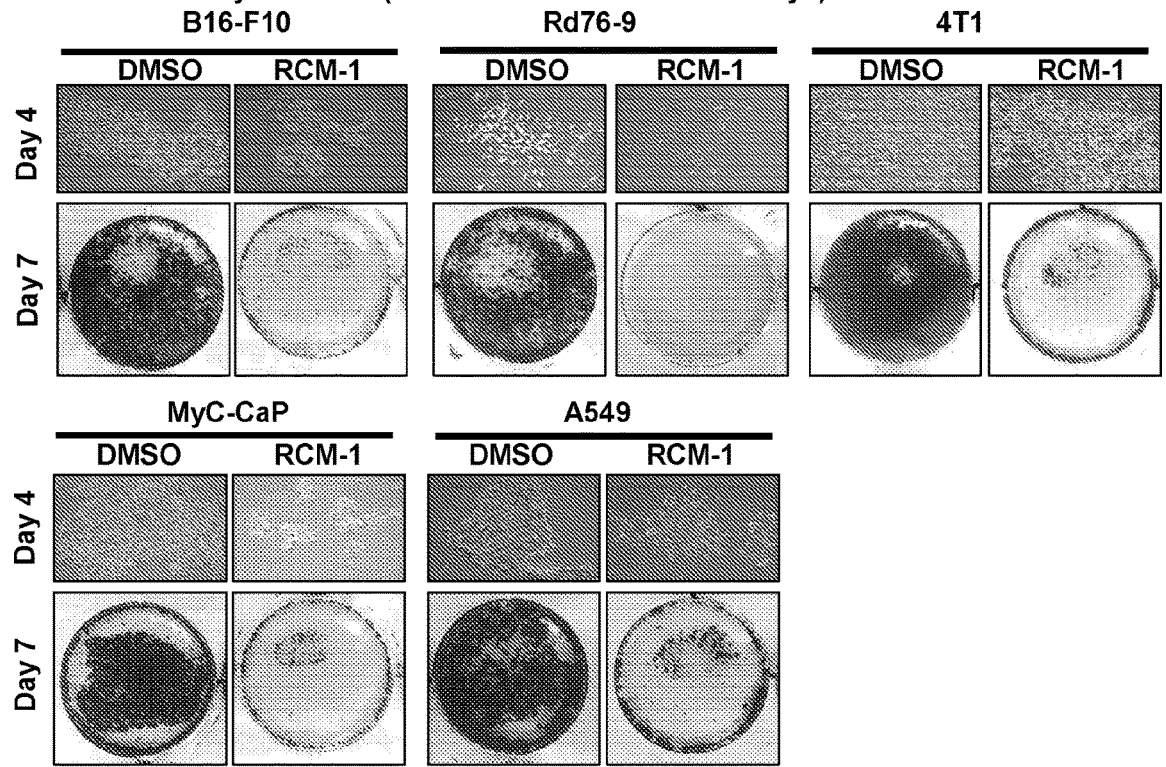
FIG. 8. RCM-1 inhibits the initiation as well as growth of cancer cell colonies in vitro. (A) Treatment with RCM-1 during initial stage of tumor colonies formation was sufficient to prevent further growth and formation of tumor colonies after RCM-1 treatment was terminated. B16-F10, Rd76-9, 4T1, MyC-CaP and A549 cells were seeded in 6-well plates and treated with 20 μM RCM-1 the same day. DMSO-treated cells were used as controls. The RCM-1 was removed after 72 h and cells were incubated for another 3 days in media without RCM-1. The colonies were fixed and stained with 0.5% crystal violet. The images are representative of three independent experiments. (B) Initiation of RCM-1 treatment after the tumor cell colonies were already formed was sufficient to inhibit the further growth of tumor cell colonies. 5×10³ of A549, B16-F10, Rd76-9, 4T1 and MyC-CaP tumor cells were seeded in 6-well plates and incubated for 72 h and then treated with either DMSO or RCM-1 (20 μM). The cells were incubated for another 3 days and the colonies were fixed and stained with 0.5% crystal violet. RCM-1 inhibits growth of pre-existing tumor colonies. The results were obtained from three independent experiments.
Figure 8:
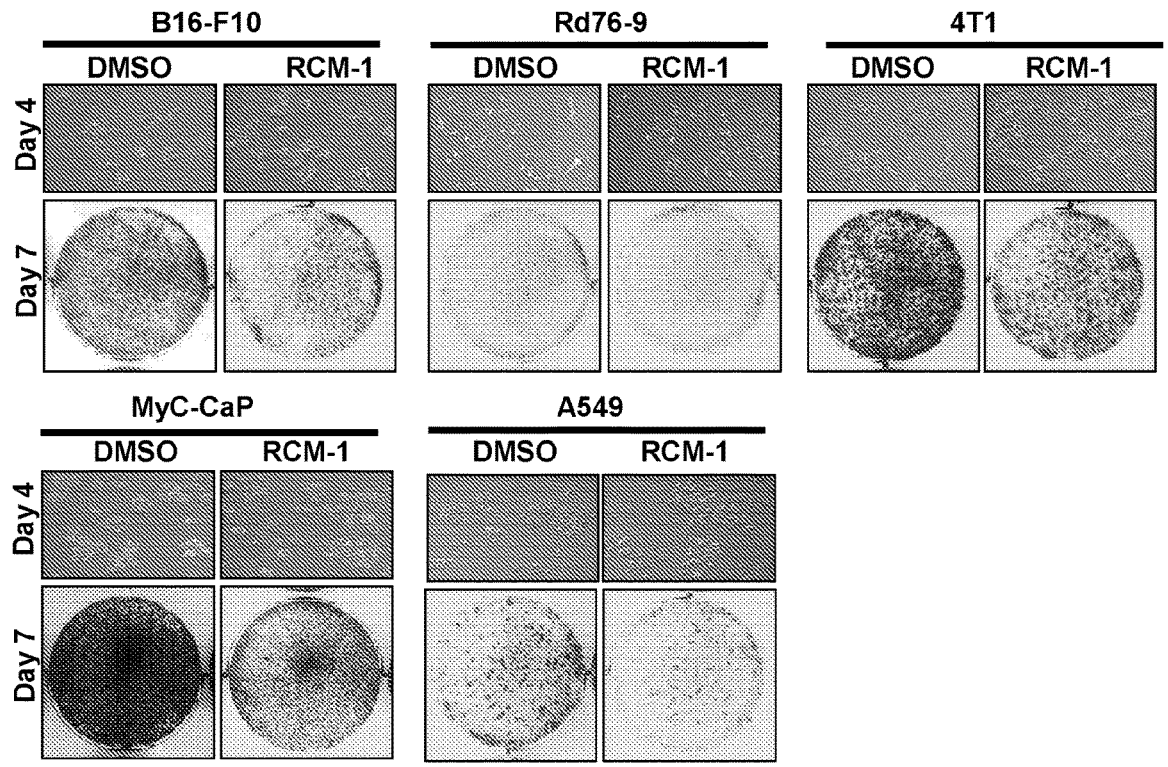
Figure 9:
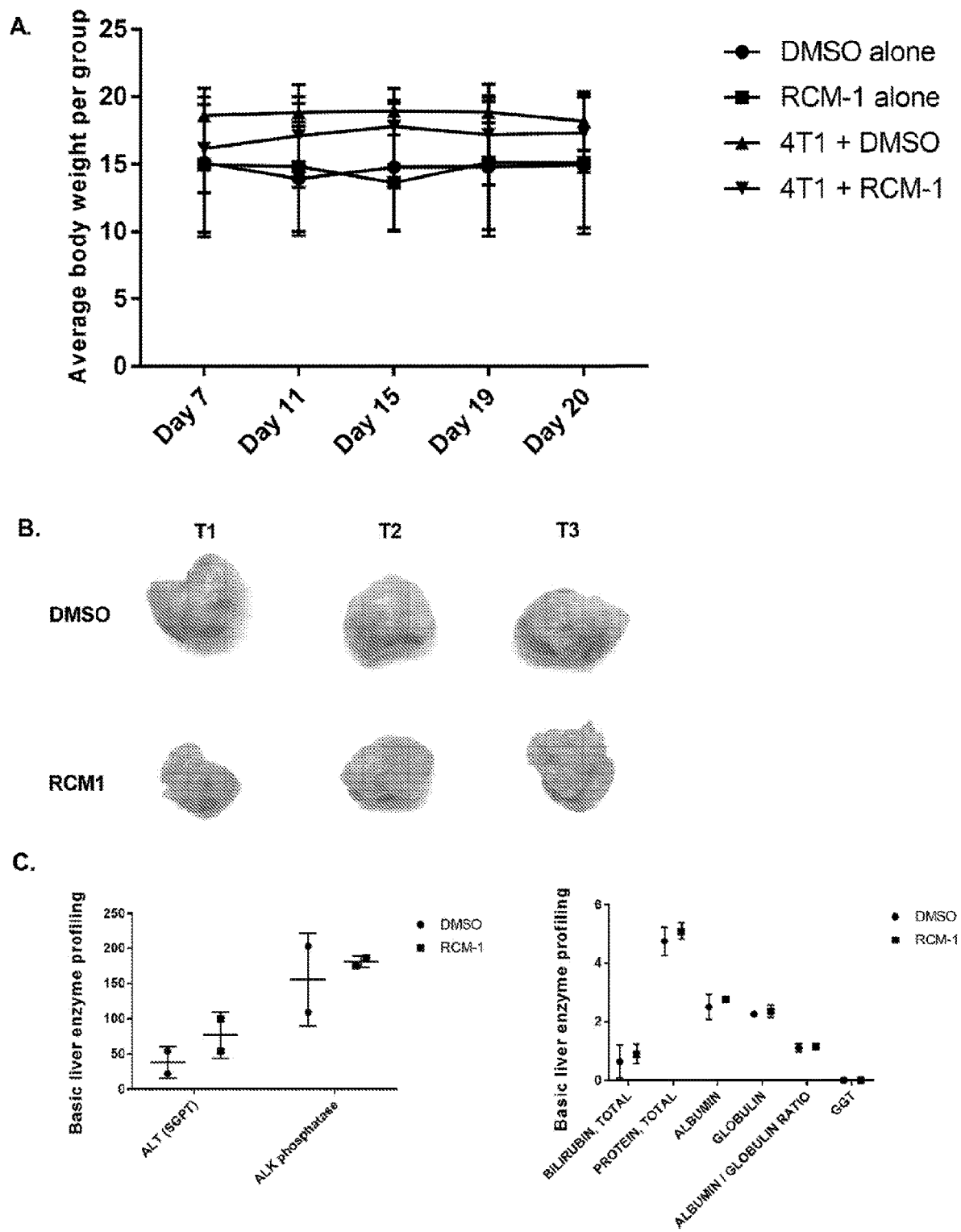
FIG. 9. RCM-1 treatment is not-toxic and does not change body weights or the liver metabolic enzymes in the blood serum of treated mice. Balb/C mice were inoculated with 4T1 breast adenocarcinoma tumor cells and treated with RCM-1 for 20 days (every other day starting at day 10 after inoculation of tumor cells). DMSO-treated mice were used as controls. (A) The graph shows the average body weight of 4T1-tumor bearing Balb/C mice after RCM-1 or DMSO treatment. (B) The image shows the tumor sizes of DMSO- or RCM-1 treated mice. (C) The graph shows metabolic liver enzymes panel the serum of DMSO- or RCM-1-treated mice.
Figure 10:
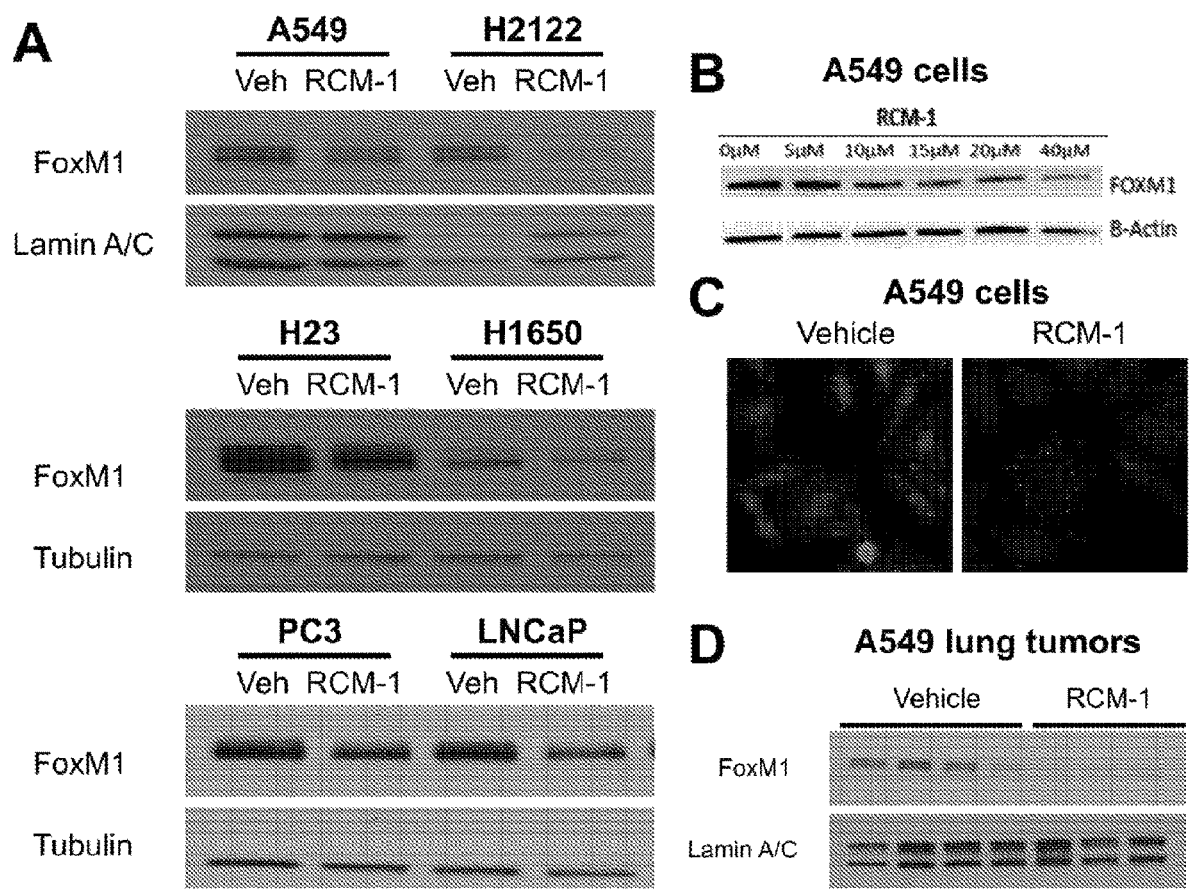
FIG. 10. RCM-1 small molecule compound decreases FOXM1 protein in tumor cells. (A) Western blot analysis shows a reduction of FOXM1 protein in RCM-1-treated human lung adenocarcinoma cells (A549, H2122, H23 and H1650) and prostate tumor cells (PC3 and LNCaP). RCM-1 was given in concentration of 20 μM for 24 hours. Lamin A/C and tubulin were used as loading controls. (B) A dose-response curve showing the inhibition of FOXM1 by RCM-1 in A549 cells. (C) Immunostaining of A549 cells with anti-FOXM1 antibodies (red fluorescence) shows decreased FOXM1 staining in RCM-1-treated cells. RCM-1 (20 μM in 0.1% of DMSO) or vehicle (0.1% of DMSO) was added to the cell cultures for 24 hours. (D) RCM-1 was given to immunocompromised mice bearing orthotopic lung tumor transplants of human A549 adenocarcinoma cells. Western blot shows that RCM-1 inhibits FOXM1 in lung tissue of tumor-bearing mice. Each line represents individual mice.

Given a critical need for new therapeutic approaches to treat human cancers, Applicant has identified RCM-1 compound as a novel inhibitor of FOXM1. Studies with tumor cell lines demonstrated that RCM-1 inhibited protein levels of FOXM1 and reduced FOXM1 content in tumor cells. These cell lines include rhabdomyosarcoma, melanoma, lung adenocarcinoma, prostate carcinoma, pancreatic adenocarcinoma and breast carcinoma cell lines (FIG. 4 and FIG. 10). In particular, Applicant has found that RCM-1 reduced total protein levels of FOXM1 and FOXM1 immunostaining in nuclei of Rd76-9 rhabdomyosarcoma, B16-F10 melanoma, MyC-CaP, PC3, and LNCaP prostate carcinoma (see FIG. 10), KPC-2 pancreatic carcinomas, A549, H2122, H23, and H1650 lung adenocarcinomas (see FIG. 10) and 4T1 breast carcinoma cells treated in culture (FIG. 4 and FIG. 10). A549 and H122 lung adenocarcinoma cells and KPC-2 pancreatic carcinoma cells have activated Kras mutation and represent the most aggressive type of carcinomas. Applicant has found that RCM-1 treatment reduced cellular proliferation and increased duration of cell cycle and mitosis in these cancer cell lines (FIG. 5). RCM-1 treatment reduced the ability of tumor cells to form colonies and to migrate, two major characteristics of cancer cells (FIG. 6-8).

Figure 2:
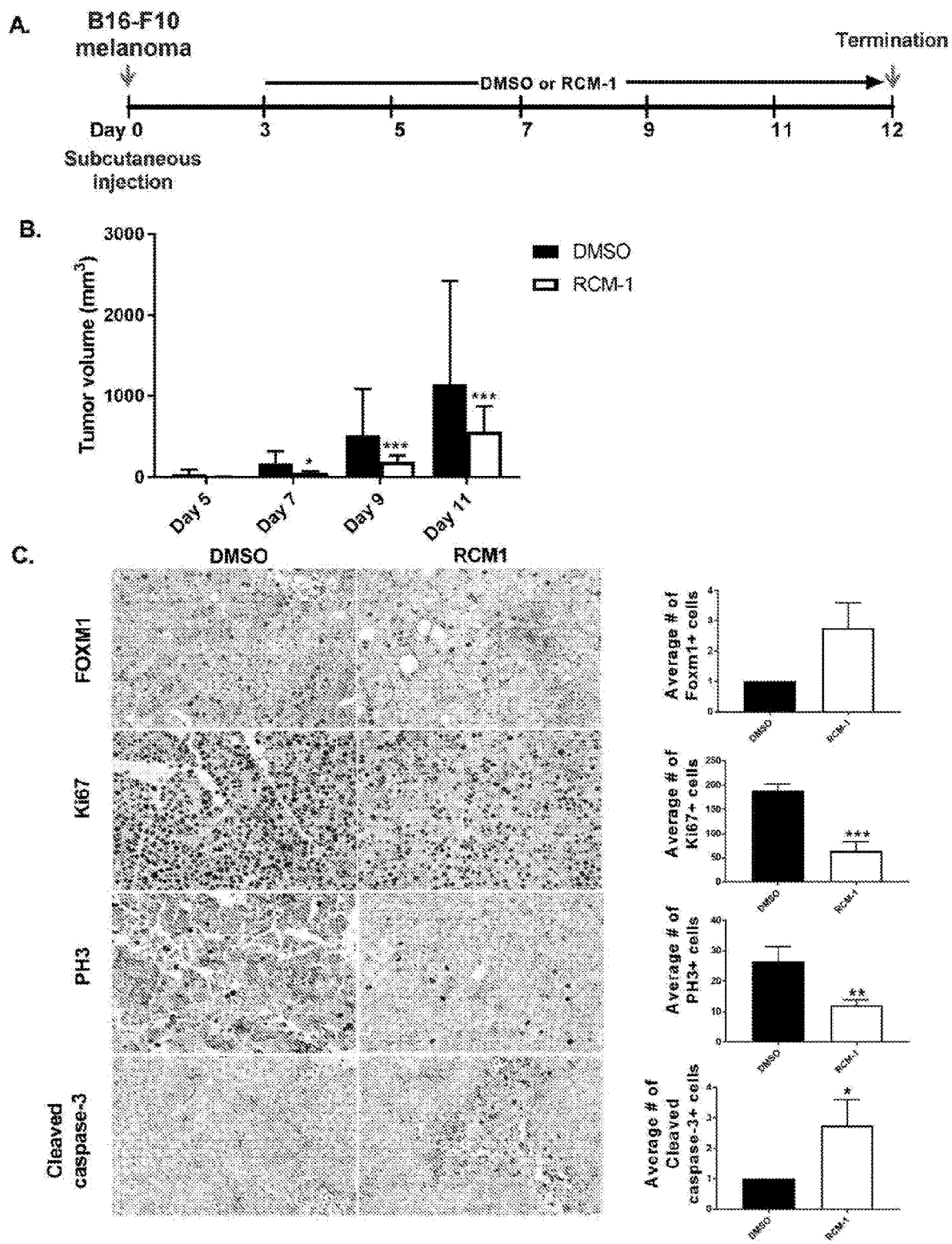
FIG. 2. RCM-1 treatment reduces growth of the B16-F10 melanoma tumors in mice. (A) Schematic representation of the experimental protocol. Mouse B16-F10 melanoma cells (1×106 cells) were injected subcutaneously in C56B1/6J mice (n=7 animals per grpoup). Three days after the tumor cell inoculation, 40 µL of either Vehicle (DMSO) or RCM1 (20 mg/Kg body weight) were injected intraperitoneally in the animals every other day. The animals were sacrificed and tumors were harvested on day 12. (B) RCM-1 decreased the B16-F10 tumor growth as compared to the Vehicle-treated group. The graph shows the average tumor volume per group with or without RCM1 treatment presented as mean±SD. *$p<0.05$, $p<0.01$ and *$p<0.001$ compared to the DMSO-treated control group. (C) RCM-1 treatment decreased tumor cell proliferation and increased apoptosis in B16-F10 melanoma tumors. Paraffin-embedded sections of DMSO- or RCM-1-treated B16-F10 tumors were stained with antibodies against FOXM1, Ki67, PH3 and Cleaved caspase-3 (magnification ×200). The RCM-1-treated B16-F10 tumors showed significantly reduced immune-labeling of proliferation markers Ki67 and PH3. Staining for Cleaved caspase-3 (labeling apoptotic cells) was increased in RCM-1-treated tumors. The graphs in the right panel show the average numbers of FOXM1-, Ki67-, PH3- and Cleaved caspase-3-positive cells in each group. Positive cells (dark brown) were counted in 5 random microscopic fields per group and the numbers are presented as mean±SD. *$p<0.05$, $p<0.01$ and *$p<0.001$ compared to the DMSO-treated control group.
Figure 3:
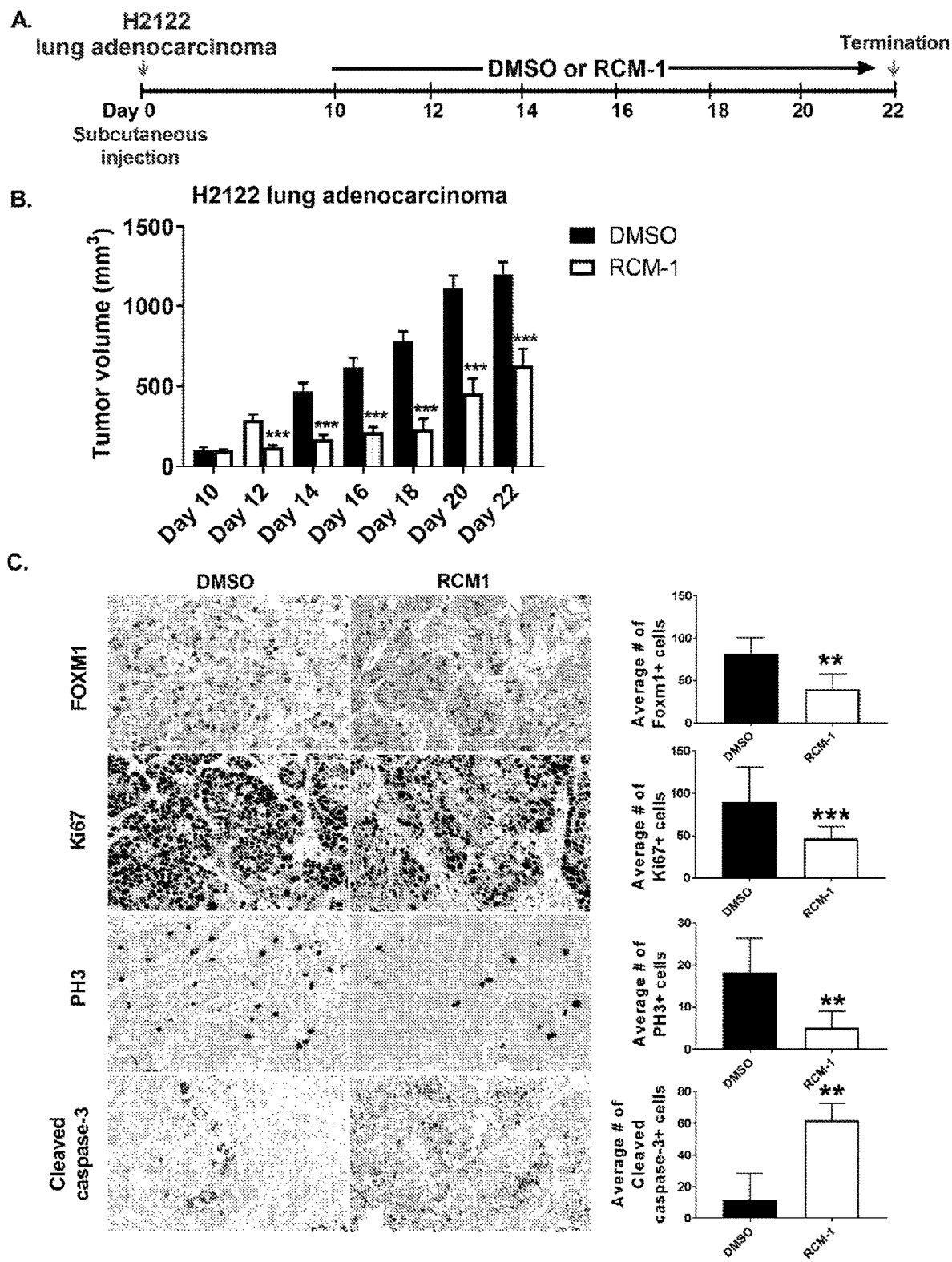
FIG. 3. RCM-1 treatment reduces growth of the human H2122 lung adenocarcinoma in mice. (A) Schematic representation of the experimental protocol. H2122 cells (1×106 cells) were injected subcutaneously in the flanks of NSG-SCID mice (n=5 animals per group). Ten days after H2122 cell inoculation, 40 µL of either Vehicle (DMSO) or RCM1 (20 mg/Kg body weight) were injected intraperitoneally in the animals every other day until the end of the experiment. Animals were sacrificed and tumors were harvested on day 22. (B) RCM-1 decreased the H2122 tumor growth compared to the vehicle group. The graph shows the average tumor volume per group with or without RCM1 treatment and is presented as mean±SD. *p<0.05, p<0.01 and *p<0.001 compared to the DMSO-treated control group. (C) RCM-1 decreased tumor cell proliferation and increased apoptosis in H2122 tumors. Paraffin-embedded sections of Vehicle- or RCM-1-treated tumors were stained with antibodies against FOXM1, Ki67, PH3 and Cleaved caspase-3, respectively (magnification ×200). The RCM-1-treated H2122 tumors showed reduced FOXM1 staining and decreased expression of proliferation-specific markers Ki67 and PH3. Cleaved caspase staining was increased in the RCM-1 treated tumors, indicating an increase in apoptosis. The right panels show the average numbers of FOXM1-, Ki67-, PH3- and Cleaved caspase-3-positive cells. Positive cells (dark brown) were counted in 5 random microscopic fields per group and the numbers are presented as mean±SD. *p<0.05, p<0.01 and *p<0.001 compared to the Vehicle-treated control group.

Applicant has further found that RCM-1 decreased growth of tumors in mice, including rhabdomyosarcoma, melanoma and lung adenocarcinoma (FIGS. 1B, 2B and 3B). Treatment with RCM-1 decreased FOXM1 levels in tumors, decreased proliferation of tumor cells and increased apoptosis in tumors of RCM1-treated mice (FIGS. 1C, 2C and 3C), suggesting that RCM-1 compound can be used in mouse cancer models to inhibit FOXM1 and decrease tumor growth.

There are three RAS genes in human: KRAS, HRAS, and NRAS. The instant invention may be useful for the treatment of cancers that are characterized by having a KRAS mutation, for example, or any other RAS mutation. Mutated RAS is present in 30% of all human tumors, appearing in 90% of pancreatic, 45% of colon and 35% of lung cancers. The high frequency of RAS mutations is making RAS pathway to be one of the important drug targets in oncology. FOXM1 is downstream of Kras, and depletion of FOXM1 inhibits Kras signaling pathway and non-small lung cancers in animal models. Targeted therapy against mutant RAS proteins is not available and targeting Kras downstream targets, such as Raf, MEK and ERK, has shown no significant clinical benefit in Kras mutant non-small cell lung cancers (NSCLC). Based on the critical importance of FOXM1 for Kras signaling in mouse lung cancer models, inhibition of FOXM1, either alone or in combination with other anti-cancer drugs, could be beneficial for treatment of cancers with activating mutations in the Kras oncogene.

Thus, the RCM-1 compound (either alone or in combination with other anti-cancer drugs) may be used to inhibit growth and progression of FOXM1 overexpressing cancers, for example, rhabdomyosarcoma, melanoma, lung adenocarcinoma, prostate carcinoma, pancreatic carcinoma and breast carcinoma.

In one aspect, a method of treating a proliferative disorder characterized by increased expression of the FOXM1 gene is disclosed. The method may comprise the step of administering to an individual in need thereof a composition comprising

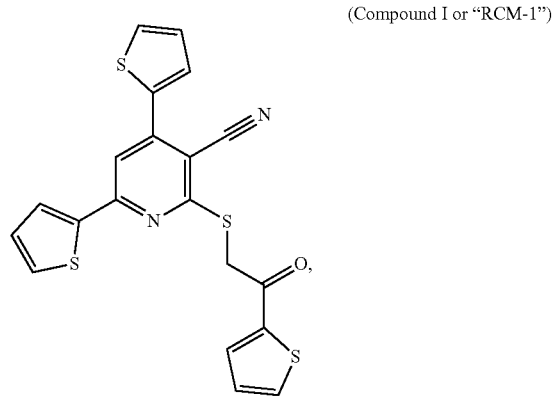 [SMILES: N#Cc1c(-c2cccs2)cc(-c2cccs2)nc1SCC(=O)c1cccs1]

(Compound I or "RCM-1")

having the formula: 2-{[2-oxo-2-(thiophen-2-yl)ethyl]sulfanyl}-4,6-di(thiophen-2-yl)pyridine-3-carbonitrile; empirical formula, C20H12N2OS4; molecular weight, 424.5874), or a pharmaceutically acceptable salt thereof. The composition may further comprise a pharmaceutically acceptable excipient.

In one aspect, the proliferative disorder may be selected from a RASopaties, a LAM disease, a fibrotic disorder, a chronic inflammatory disorder, or a cancer. In particular, the proliferative disorder may be one in which FOXM1 is overexpressed.

In one aspect, the proliferative disorder may be cancer, and may be one of an adenocarcinoma, a melanoma, a rhabdomyosarcoma, a non-small cell lung cancer (NSCLC), a head and neck squamous carcinoma, a hepatocellular carcinoma (HCC), an intrahepatic cholangiocarcinoma, a colon carcinoma, a basal cell carcinoma, an infiltrating ductal breast carcinoma, an anaplastic astrocytoma, a glioblastoma, a pancreatic carcinoma, a gastric cancer, an acute myeloid leukemia, a lung cancer, a liver cancer, a breast cancer, a prostate cancer, and a brain cancer.

In one aspect, the proliferative disorder may be selected from A549 lung adenocarcinoma and KPC-2 pancreatic carcinoma.

In one aspect, the proliferative disorder or cancer may overexpress FOXM1. The proliferative disorder or cancer may further contain a RAS mutation.

In one aspect, the composition is administered in an amount sufficient to cause one or more of the following: a decrease in tumor growth, a decrease in tumor cell proliferation, increased tumor cell apoptosis, inhibition of metastatic dissemination of cancer, improvement in patient survival, reduced ability of tumor cells to form colonies, and reduced ability of tumor cells to migrate.

In one aspect, the compound or composition may be administered to an individual in an amount sufficient to inhibit FOXM1 expression in cells overexpressing FOXM1.

In one aspect, a method of reducing the amount of a chemotherapeutic agent administered to an individual in need thereof is disclosed. The method may comprise the step of administering a composition as disclosed herein, to the individual, prior to, concurrently with, or following administration of a chemotherapeutic agent. The chemotherapeutic agent may be, for example, selected from a class of chemotherapeutic agents selected from taxanes (Paclitaxel, Docetaxel, etc), platinum-based agents (Carboplatin, Cisplatin, etc), anthracyclines (Doxorubicin, Epirubicin, etc), alkylating agents (Cyclophosphamide, Chlorambucil, etc), vinca alkaloids (Vinblastine, Vincristin, etc), epothilones, histone deacetylase inhibitors, topoisomerase I and II inhibitors, kinase inhibitors, nucleotide analogs, precursor analogs, peptide antibiotics, and combinations thereof. Such agents are known in the art and are described in, for example, Lind, M. J. Principles of cytotoxic chemotherapy, Medicine, Volume 36, Issue 1, January 2008, Pages 19-23, https://doi.org/10.1016/j.mpmed.2007.10.003; Malhotra V. and Perry M. C. Classical chemotherapy: mechanisms, toxicities and the therapeutic window. Cancer Biol Ther. 2003 July-August; 2(4 Suppl 1): S2-4; Kwak E. L., Clark J. W. and Chabner B. Targeted agents: the rules of combination. Clin Cancer Res. 2007 Sep. 15; 13(18 Pt 1): 5232-5237.

In one aspect, a composition comprising Compound 1, or a pharmaceutically acceptable salt thereof, and one or more chemotherapeutic agent selected from a taxane (Paclitaxel, Docetaxel, etc), a platinum-based agent (Carboplatin, Cisplatin, etc), anthracyclines (Doxorubicin, Epirubicin, etc), an alkylating agent (Cyclophosphamide, Chlorambucil, etc), vinca alkaloids (Vinblastine, Vincristin, etc), an epothilone, a histone deacetylase inhibitor, a topoisomerase I or II inhibitor, a kinase inhibitor, a nucleotide analog, a precursor analog, a peptide antibiotic, and combinations thereof, is disclosed.

In one aspect, a kit comprising any composition as described herein, is disclosed. The kit may further comprise a means for delivery of the composition to a human.

In one aspect, an article of manufacture is disclosed. Such article may comprise a container comprising a label; and a composition as disclosed herein. The label may indicate that the composition may be to be administered to a human having, suspected of having, or at risk for developing any proliferative disorder as disclosed herein, in particular, a cancer as disclosed herein.

The article of manufacture may further comprise one or more additional therapeutic agents selected from a taxane (Paclitaxel, Docetaxel, etc.), a platinum-based agent (Carboplatin, Cisplatin, etc.), anthracyclines (Doxorubicin, Epirubicin, etc.), an alkylating agent (Cyclophosphamide, Chlorambucil, etc.), vinca alkaloids (Vinblastine, Vincristin, etc.), an epothilone, a histone deacetylase inhibitor, a topoisomerase I inhibitor, a topoisomerase II inhibitor, a kinase inhibitor, a nucleotide analog, a precursor analog, a peptide antibiotic, and combinations thereof.

Dosage

As will be apparent to those skilled in the art, dosages outside of these disclosed ranges may be administered in some cases. Further, it is noted that the ordinary skilled clinician or treating physician will know how and when to interrupt, adjust, or terminate therapy in consideration of individual patient response.

In some aspects, the dosage of the composition provided herein, based on weight of the active compound or pharmaceutically acceptable salt thereof, administered to a subject may be about 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject may be a unit dose of about 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg. The dosage will be such that one or more of the aforementioned desired outcomes can be achieved over a period of time.

The described active may be present in combination with one or more excipients to form a composition. In one aspect, the active ingredient or a pharmaceutically acceptable salt thereof, may be present in an amount of from about 0.5% to about 95%, or from about 1% to about 90%, or from about 2% to about 85%, or from about 3% to about 80%, or from about 4%, about 75%, or from about 5% to about 70%, or from about 6%, about 65%, or from about 7% to about 60%, or from about 8% to about 55%, or from about 9% to about 50%, or from about 10% to about 40%, by weight of the composition.

A dosage regimen will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect. The effective amount of a drug required to prevent, counter, or arrest progression of a condition can be readily determined by an ordinarily skilled physician A composition or formulation may be administered to a subject continuously or periodically.

The dosage of the one or more of the disclosed active agents or a pharmaceutically acceptable salt thereof used to achieve a therapeutic effect will depend not only on such factors as the age, weight and sex of the patient and mode of administration, but also on the degree of inhibition desired and the potency of the one or more of the disclosed active agents or a pharmaceutically acceptable salt thereof for the particular disorder or disease concerned. It is also contemplated that the treatment and dosage of the one or more of the disclosed active agents or a pharmaceutically acceptable salt thereof may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect. Routes of Administration Any suitable route of administration can be employed for providing the patient with an effective dosage of the disclosed compositions. For example, oral, rectal, transdermal, parenteral (subcutaneous, intramuscular, intravenous), intrathecal, topical, inhalable (bronchial), and like forms of administration can be employed. Administration of medicaments prepared from the compounds described herein can be by any suitable method capable of introducing the compounds into the bloodstream. In some embodiments, the formulations can contain a mixture of active compounds with pharmaceutically acceptable carriers or diluents known to those of skill in the art.

Dosage Forms

The compositions may be administered in oral dosage forms such as tablets, capsules (each of which includes sustained release or timed-release formulations), pills, powders, granules, elixirs, tinctures, suspensions, syrups, and emulsions. They may also be administered in intravenous (bolus or infusion), intraperitoneal, subcutaneous, or intramuscular forms all utilizing dosage forms well known to those of ordinary skill in the pharmaceutical arts. The compositions may be administered by intranasal route via topical use of suitable intranasal vehicles, or via a transdermal route, for example using conventional transdermal skin patches, or via a bronchial route. A dosage protocol for administration using a transdermal delivery system may be continuous rather than intermittent throughout the dosage regimen. The compositions may be also delivered in complexes with nanoparticle carriers via intravenous, intratracheal or intranasal routes.

In certain aspects, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. Oral preparations include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. For topical or nasal administration, penetrants or permeation agents that are appropriate to the particular barrier to be permeated are used in the formulation. Such penetrants are generally known in the art. The pharmaceutical compositions are prepared by conventional techniques appropriate to the desired preparation containing appropriate amounts of the active ingredient, that is, one or more of the disclosed active agents or a pharmaceutically acceptable salt thereof according to the invention.

The compositions can be prepared in any desired form, for example, tablets, powders, capsules, injectables, suspensions, sachets, cachets, patches, solutions, elixirs, and aerosols. Carriers such as starches, sugars, microcrystalline cellulose, diluents, granulating agents, lubricants, binders, disintegrating agents, and the like can be used in oral solid preparations. In certain embodiments, the compositions are prepared as oral solid preparations (such as powders, capsules, and tablets). In certain embodiments, the compositions are prepared as oral liquid preparations. In some embodiments, the oral solid preparations are tablets. If desired, tablets can be coated by standard aqueous or non-aqueous techniques.

In addition to the dosage forms set out above, the compounds disclosed herein can also be administered by sustained release, delayed release, or controlled release compositions and/or delivery devices.

Pharmaceutical compositions suitable for oral administration can be provided as discrete units such as capsules, cachets, sachets, patches, injectables, tablets, and aerosol sprays, each containing predetermined amounts of the active ingredients, as powder or granules, or as a solution or a suspension in an aqueous liquid, a non-aqueous liquid, an oil-in-water emulsion, or a water-in-oil liquid emulsion. Such compositions can be prepared by any of the conventional methods of pharmacy, but the majority of the methods typically include the step of bringing into association the active ingredients with a carrier which constitutes one or more ingredients. In general, the compositions are prepared by uniformly and intimately admixing the active ingredients with liquid carriers, finely divided solid carriers, or both, and then, optionally, shaping the product into the desired presentation.

For example, a tablet can be prepared by compression or molding, optionally, with one or more additional ingredients. Compressed tablets can be prepared by compressing in a suitable machine the active ingredient in a free-flowing form such as powder or granules, optionally mixed with a binder, lubricant, inert diluent, surface active or dispersing agent. Molded tablets can be made by molding, in a suitable machine, a mixture of the powdered compound moistened with an inert liquid diluent.

The compositions or fractions thereof may comprise suitable pharmaceutical diluents, excipients, vehicles, or carriers selected based on the intended form of administration, and consistent with conventional pharmaceutical practices. The carriers, vehicles etc. may be adapted to provide an additive, synergistically effective or therapeutically effective amount of the active compounds. By way of example, for oral administration in the form of a capsule or tablet, the active components can be combined with an oral, non-toxic pharmaceutically acceptable inert carrier such as lactose, starch, sucrose, methyl cellulose, magnesium stearate, glucose, calcium, sulfate, dicalcium phosphate, mannitol, sorbital, and the like. For oral administration in a liquid form, the agents may be combined with any oral, non-toxic, pharmaceutically acceptable inert carrier such as ethanol, glycerol, water, and the like. Suitable binders (e.g. gelatin, starch, corn sweeteners, natural sugars including glucose; natural and synthetic gums, and waxes), lubricants (e.g.

sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof.

Formulations for parenteral administration of a composition may include aqueous solutions, syrups, aqueous or oil suspensions and emulsions with edible oil such as cottonseed oil, coconut oil or peanut oil. Dispersing or suspending agents that can be used for aqueous suspensions include synthetic or natural gums, such as tragacanth, alginate, acacia, dextran, sodium carboxymethylcellulose, gelatin, methylcellulose, and polyvinylpyrrolidone.

Compositions for parenteral administration may include sterile aqueous or non-aqueous solvents, such as water, isotonic saline, isotonic glucose solution, buffer solution, or other solvents conveniently used for parenteral administration of therapeutically active agents. A composition intended for parenteral administration may also include conventional additives such as stabilizers, buffers, or preservatives, e.g. methylhydroxybenzoate or similar additives.

In one aspect, a solid form pharmaceutical composition is provided (e.g. tablets, capsules, powdered, or pulverized form) comprising one or more of the disclosed active agents or salt thereof.

In one aspect, a liquid drug formulation is provided and comprises a pharmaceutically acceptable salt of one or more of the disclosed active agents or salt thereof, and to lyophilized drug formulations that can be reconstituted to provide suspensions that are stable and suitable for parenteral administration.

A composition described herein may be sterilized by, for example, filtration through a bacteria retaining filter, addition of sterilizing agents to the composition, irradiation of the composition, or heating the composition. Alternatively, the compounds and compositions may be provided as sterile solid preparations e.g. lyophilized powder, which are readily dissolved in sterile solvent immediately prior to use.

Kits

In one aspect, kits are disclosed. A kit may comprise, for example, a composition comprising the aforementioned RCM-1 Compound and a pharmaceutically acceptable carrier; and a means for delivery of the composition to an individual.

Further disclosed is an article of manufacture comprising a container comprising a label; and a composition comprising a compound as disclosed herein, wherein the label may indicate that the composition may be to be administered to an individual having, suspected of having, or at risk for developing, a disease or disorder as disclosed herein, in particular, a cancer, or a cancer overexpressing the FOXM1 gene, as described herein.

In one aspect, a kit comprises or consists essentially of agents or compositions described herein. The kit may be a package that houses a container which may contain a composition as disclosed herein, and also houses instructions for administering the agent or composition to a subject. In one aspect, a pharmaceutical pack or kit may be provided comprising one or more containers filled with one or more composition as disclosed herein. Associated with such container(s) can be various written materials such as instructions for use, or a notice in the form prescribed by a governmental agency regulating the manufacture, use or sale of pharmaceuticals or biological products, which notice reflects approval by the agency of manufacture, use, or sale for human administration. The kit may comprise a label, such labeling may include amount, frequency, and method of administration.

As there may be advantages to mixing a component of a composition described herein and a pharmaceutically acceptable carrier, excipient or vehicle near the time of use, kits in which components of the compositions are packaged separately are disclosed. For example, the kit may contain an active ingredient in a powdered or other dry form in, for example, a sterile vial or ampule and, in a separate container within the kit, a carrier, excipient, or vehicle, or a component of a carrier, excipient, or vehicle (in liquid or dry form). In an aspect, the kit can contain a component in a dry form, typically as a powder, often in a lyophilized form in, for example, a sterile vial or ampule and, in a separate container within the kit, a carrier, excipient, or vehicle, or a component of a carrier, excipient, or vehicle. Alternatively, the kit may contain a component in the form of a concentrated solution that may be diluted prior to administration. Any of the components described herein, any of the carriers, excipients or vehicles described herein, and any combination of components and carriers, excipients or vehicles can be included in a kit.

Optionally, a kit may also contain instructions for preparation or use (e.g., written instructions printed on the outer container or on a leaflet placed therein) and one or more devices to aid the preparation of the solution and/or its administration to a patient (e.g., one or a plurality of syringes, needles, filters, tape, tubing (e.g., tubing to facilitate intravenous administration) alcohol swabs and/or the Band-Aid® applicator). Compositions which are more concentrated than those administered to a subject can be prepared. Accordingly, such compositions can be included in the kits with, optionally, suitable materials (e.g., water, saline, or other physiologically acceptable solutions) for dilution. Instructions included with the kit can include, where appropriate, instructions for dilution.

In other aspects, the kits can include pre-mixed compositions and instructions for solubilizing any precipitate that may have formed during shipping or storage. Kits containing solutions of one or more of the disclosed active agents, or a pharmaceutically acceptable salt thereof, and one or more carriers, excipients or vehicles may also contain any of the materials mentioned above (e.g., any device to aid in preparing the composition for administration or in the administration per se). The instructions in these kits may describe suitable indications (e.g., a description of patients amenable to treatment) and instructions for administering the solution to a patient.

Materials and Methods

Cell Culture

All the cancer cell lines including human lung adenocarcinoma A549 and H2122, mouse lung adenocarcinoma LLC, mouse melanoma B16-F10, mouse rhabdomyosarcoma Rd76-9, mouse mammary carcinoma 4T1 and mouse prostate cancer MyC-CaP cells were obtained from American Type Culture Collection (ATCC, Manassas, Va.). Cells were cultured and maintained in RPMI-1640 medium (Sigma-Aldrich, St. Louis, Mo.) supplemented with 10% FBS (Sigma Aldrich) and 1% anti-biotic anti-mycotic solution (Sigma-Aldrich). All the cells were grown in a humidified atmosphere at 37° C. with 5% CO2. The compound RCM-1 (2-{[2-oxo-2-(thiophen-2-yl)ethyl]sulfanyl}-4,6-di(thiophen-2-yl)pyridine-3-carbonitrile) was synthesized by Vitas-M Laboratory (95% purity). RCM-1 was dissolved in DMSO at a stock concentration of 20 mM and was given to mice intraperitoneally.

Mouse Models

All the animals were procured from Jackson Laboratory (Bar Harbor, Me., USA) and the study was conducted according to the guidelines as well as protocol approved by the Institutional Animal Care and Use Committee (IACUC) of Cincinnati Children's Hospital. Animals were given one week for acclimatization before starting the experiment.

For human lung adenocarcinoma H2122 orthotopic tumor model, $1 \times 10^6$ H2122 cells were injected subcutaneously into 6-8 weeks old Nod-Scid-Gamma (NSG) anesthetized mice (Jackson Laboratory). Mice were then randomly divided into two groups (n=5 each). The two animal groups were injected intraperitoneally (i.p.) with equal volumes of (40 µL) of either Vehicle (DMSO) or RCM-1 (20 mg/Kg body weight) every alternate day starting from day 10, when there were visible tumors formed. Tumor volumes (mm3) were measured every alternate day using a digital caliper. The animals were sacrificed and tumors were harvested on day 22. Lung tumor tissues from each group were divided equally for snap-freezing or for fixing in 4% paraformaldehyde for histopathological analyses.

For syngeneic B16-F10 melanoma induction, $1 \times 10^6$ B16-F10 cells were injected subcutaneously in animals of each of the two animal groups (n=7 each). Equal volumes (40 µL) of either Vehicle (DMSO) or RCM-1 (20 mg/Kg b.w.) were injected intraperitoneally in the animals every alternate day starting from day 3 after the tumor cell injections. The animals were sacrificed and tumors were harvested on day 12. Tumor volumes (mm3) were measured every alternate day using a digital caliper. The animals were sacrificed and tumors were harvested on day 12. Tumor tissues from each group were snap-frozen and fixed in 4% paraformaldehyde for histopathological analyses.

For RD-syngeneic rhabdomyosarcoma model, $1 \times 10^6$ Rd76-9 cells were injected intramuscularly in the flanks of two separate groups (n=8 each) of C56B1/6J mice. Equal volumes (40 µL) of either Vehicle (DMSO) or RCM-1 (20 mg/Kg b.w.) were injected intraperitoneally in the animals every alternate day starting from day 7 followed by the cell injections. Tumor volumes (mm3) were measured every alternate day using a digital caliper. The animals were sacrificed and tumors were harvested and weighed at day 16. Tumor samples were collected for molecular and immunohistochemical analyses.

For 4T1 syngeneic mammary carcinoma model, orthotopic injection of $1 \times 10^6$ 4T1 cells was performed in Balb/C mice (n=8 in each group). Two groups of animals were injected with 1× PBS (n=2 each). Equal volumes (40 µL) of either Vehicle (DMSO) or RCM-1 (20 mg/Kg b.w.) were injected intraperitoneally in the animals five times a week starting from day 6 till day 24. The tumor volume was measured using a caliper. On day 26, the animals were sacrificed and the tumors were harvested and weighed. Serum samples were collected from the DMSO or RCM-1 treated animals without tumor injection and submitted for serum enzyme profiling.

Immunohistochemical Staining

Formalin-fixed lung tissue sections (5 mm) were processed for immunohistochemical staining using anti-FOXM-1, anti-Ki-67, anti-PH3 (Santa Cruz Biotechnology) and anti-Cleaved Caspase-3 (Abcam) antibodies, as described previously (Balli et al., 2013). The numbers of antibody-positive cells were counted in at least 6 different microscopic fields and represented as the average number of positive cells per microscopic field.

Tumor Cell Growth Analysis

Tumor cells were seeded in triplicates ($0.35 \times 10^5$-$1 \times 10^5$ per well) in 6-well plates and incubated for 24 h. The cells were then treated with 20 µM RCM-1 and equal volume of DMSO was used as the vehicle control. The total number of viable cells were counted by trypan blue staining at 24, 48 and 72 h using an automated cell counter (Countess II FL, ThermoFisher Scientific). Experiments were performed in triplicates and presented as average fold change in live cell count ±SE.

Phase-Contrast Live Cell Imaging

Cells were grown in Nunc Delta Surface 24-well plates (ref. 142485; ThermoFisher Scientific). Images were acquired on a Leica DMI 6000 motorized inverted epifluorescence microscope under controlled temperature, atmosphere and humidity (Leica, Germany). 4 fields per well were imaged every 5 min for 2 3 days, using a 20× LD objective. Mitotic duration was measured as the interval between nuclear envelope breakdown and anaphase onset. Cell cycle duration was measured as the interval between anaphase onset of the mother cell and its daughter cells. p-values were obtained using GraphPad Prism version 6 (GraphPad, San Diego, Calif., USA). Data were tested for parametric vs. non-parametric distribution using D'Agostino-Pearson omnibus normality test. As data followed a non-parametric distribution, Mann-Whitney test was applied. ns: $p>0.05$, *$p \le 0.05$, $p<0.01$, *$p<0.001$ and ****$p<0.0001$. Values are shown as mean±SD.

Confocal Immunofluorescence Imaging

The immunofluorescence staining was performed as described previously (Balli et al., 2013). Approximately, $2 \times 10^4$ cells were seeded on sterile coverslips and treated with 20 µM of RCM-1 and incubated in CO2 incubator for 24 h. Then after, the cells were fixed in a freshly prepared 2% paraformaldehyde and auto fluorescence quenching was performed by incubating the cells with ammonium chloride at room temperature. Cells were permeabilized using 0.1% Triton X-100 and non-specific sites were blocked by incubating the cells with blocking buffer for 45 min at room temperature. The cells were then incubated with anti-FOXM1, FOXA1 and α-tubulin primary antibodies at 4° C. overnight. Following washing, the cells were incubated in appropriate fluorophore conjugated secondary antibodies (Sigma-Aldrich, 1:200) for 1 h in dark at RT. After washing, the coverslips were mounted on the slides with Prolong Gold mounting Medium with DAPI for nuclear stain. IgG controls were used as the negative controls of immunofluorescence staining. The fluorescent images of DMSO- or RCM-1-treated cells at 600× magnification were captured using Nikon A1 inverted confocal microscope.

Wound Healing Assay

The migratory capacities of A549, H2122 and 4T1 cells were assessed by in vitro wound healing assay as described previously (Milewski et al., 2017). Briefly, $2 \times 10^5$ cells per well were seeded in 6-well plates and grown to a confluency of 80-90%. A wound was created in the middle of the well by scraping with a 200 µL pipette tip and A549, H2122 and 4T1 cells were treated with different concentrations of RCM-1 and incubated for 18 h, 12 h and 18 h respectively. Wound closure photographs were captured by using a semi-automated Carl Zeiss microscope equipped with a digital camera. The wound area was measured by using ImageJ 1.51k software. The results were expressed as percent migration compared with control.

Clonogenic Assay

In vitro colony forming potentials of different cancer cells were assessed by anchorage-dependent clonogenic assay, as described previously (Kahn et al., 2006). Approximately 1×103 cancer cells were seeded into 6-well plates in triplicates. After 24 h, cells were treated with either DMSO or RCM-1 (20 µM) and were allowed to incubate at 37° C. in the CO2 incubator for 7 days. After incubation, the colonies were fixed and stained with 0.1% crystal violet (Sigma-Aldrich). The colonies with ≥50 cells were counted and expressed as average number of colonies per well.

siRNA Knockdown of FOXM1

The siRNA transfection experiments were performed as described previously (Cai et al., 2013). Approximately $2 \times 10^5$ cells per well were seeded in a 6-well plate and allowed to incubate overnight. Lyophilized siRNAs specific to human or mouse FOXM1 genes (Sigma-Aldrich) were dissolved at a stock concentration of 10 µM using RNase-free water and approximately 1 µg siRNAs were delivered to the cells using the lipofectamine reagent (Invitrogen) according to the manufacturer's protocol. Scrambled siRNA was used as a negative control to monitor knock-down efficacy and toxicity, if any. Cells were harvested and cytoplasmic and nuclear extraction was performed.

Western blot analysis. Cytoplasmic and nuclear extracts of different cancer cell lines were prepared using 1× RIPA-lysis buffer (Millipore, Billerica, Mass.). Proteins were resolved on 8-16% SDS-polyacrylamide gradient gels and transferred onto PVDF membranes (Millipore). After incubation in blocking buffer (5% skimmed milk) for 1 h, the membranes were incubated overnight with primary antibodies specific for FOXM1, b-actin, Lamin A/C or tubulin. The blots were then incubated with specific HRP-conjugated secondary antibodies and bands were visualized using ECL (Santa Cruz) on ImageQuant LAS4000 chemiluminescence detection system (GE Healthcare, Amarsham, UK). The band intensities were quantified using ImageJ 1.51k software.

Statistical analysis. Statistical analysis was performed using GraphPad Prism (GraphPad Software, Inc., La Jolla, Calif., USA). ANOVA and Student's T-test were used to determine statistical significance. Right skewed measurements were log-transformed to meet normality assumption prior to analysis. P values less than 0.05 were considered significant. Values for all measurements were expressed as the mean±standard deviation (SD).

REFERENCES

1. C. Pilarsky, M. Wenzig, T. Specht, H. D. Saeger, R. Grutzmann, Identification and validation of commonly overexpressed genes in solid tumors by comparison of microarray data. *Neoplasia* 6, 744-750 (2004).
2. I. M. Kim, T. Ackerson, S Ramakrishna, M. Tretiakova, I. C. Wang, T. V. Kalin, M. L. Major, G. A. Gusarova, H. M. Yoder, R. H. Costa, V. V. Kalinichenko, The Forkhead Box m1 Transcription Factor Stimulates the Proliferation of Tumor Cells during Development of Lung Cancer. *Cancer Res.* 66, 2153-2161. (2006).
3. J. S. Lee, I. S. Chu, J. Heo, D. F. Calvisi, Z. Sun, T. Roskams, A. Durnez, A. J. Demetris, S. S. Thorgeirsson, Classification and prediction of survival in hepatocellular carcinoma by gene expression profiling. *Hepatology* 40, 667-676. (2004).
4. M. T. Teh, S. T. Wong, G. W. Neill, L. R. Ghali, M. P. Philpott, A. G. Quinn, FOXM1 Is a Downstream Target of Gli1 in Basal Cell Carcinomas. *Cancer research* 62, 4773-4780. (2002).
5. Y. Yoshida, I. C. Wang, H. M. Yoder, N. O. Davidson, R. H. Costa, The forkhead box M1 transcription factor contributes to the development and growth of mouse colorectal cancer. *Gastroenterology* 132, 1420-1431 (2007).
6. S. S. Myatt, E. W. Lam, The emerging roles of forkhead box (Fox) proteins in cancer. *Nature reviews* 7, 847-859 (2007).
7. V. V. Kalinichenko, M. Major, X. Wang, V. Petrovic, J. Kuechle, H. M. Yoder, B. Shin, A. Datta, P. Raychaudhuri, R. H. Costa, Forkhead Box m1b Transcription Factor is Essential for Development of Hepatocellular Carcinomas and is Negatively Regulated by the p19ARF Tumor Suppressor. *Genes & development* 18, 830-850. (2004).
8. Q. Li, N. Zhang, Z. Jia, X. Le, B. Dai, D. Wei, S. Huang, D. Tan, K. Xie, Critical role and regulation of transcription factor FoxM1 in human gastric cancer angiogenesis and progression. *Cancer research* 69, 3501-3509 (2009).
9. E. Gemenetzidis, A. Bose, A. M. Riaz, T. Chaplin, B. D. Young, M. Ali, D. Sugden, J. K. Thurlow, S. C. Cheong, S. H. Teo, H. Wan, A. Waseem, E. K. Parkinson, F. Fortune, M. T. Teh, FOXM1 upregulation is an early event in human squamous cell carcinoma and it is enhanced by nicotine during malignant transformation. *PloS one* 4, e4849 (2009).
10. S. Nakamura, I. Hirano, K. Okinaka, T. Takemura, D. Yokota, T. Ono, K. Shigeno, K. Shibata, S. Fujisawa, K. Ohnishi, The FOXM1 transcriptional factor promotes the proliferation of leukemia cells through modulation of cell cycle progression in acute myeloid leukemia. *Carcinogenesis* 31, 2012-2021 (2010).
11. T. V. Kahn, V. Ustiyan, V. V. Kalinichenko, Multiple faces of FoxM1 transcription factor: lessons from transgenic mouse models. *Cell cycle* (Georgetown, Tex. 10, 396-405 (2011).
12. BALLI, D., USTIYAN, V., ZHANG, Y., WANG, I. C., MASINO, A. J., REN, X., WHITSETT, J. A., KALINICHENKO, V. V. & KALIN, T. V. 2013. Foxm1 transcription factor is required for lung fibrosis and epithelial-to-mesenchymal transition. EMBO J, 32, 231-44.
13. BALLI, D., ZHANG, Y., SNYDER, J., KALINICHENKO, V. V. & KALIN, T. V. 2011. Endothelial cell-specific deletion of transcription factor FoxM1 increases urethane-induced lung carcinogenesis. Cancer Res, 71, 40-50.
14. BEHREN, A., MUHLEN, S., ACUNA SANHUEZA, G. A., SCHWAGER, C., PLINKERT, P. K., HUBER, P. E., ABDOLLAHI, A. & SIMON, C. 2010. Phenotype-assisted transcriptome analysis identifies FOXM1 downstream from Ras-MKK3-p38 to regulate in vitro cellular invasion. Oncogene, 29, 1519-30.
15. BHAT, U. G., HALASI, M. & GARTEL, A. L. 2009. Thiazole antibiotics target FoxM1 and induce apoptosis in human cancer cells. PLoS ONE, 4, e5592.
16. CAI, Y., BALLI, D., USTIYAN, V., FULFORD, L., HILLER, A., MISETIC, V., ZHANG, Y., PALUCH, A. M., WALTZ, S. E., KASPER, S. & KALIN, T. V. 2013. Foxm1 expression in prostate epithelial cells is essential for prostate carcinogenesis. J Biol Chem, 288, 22527-41.
17. CARTER, S. L., EKLUND, A. C., KOHANE, I. S., HARRIS, L. N. & SZALLASI, Z. 2006. A signature of chromosomal instability inferred from gene expression profiles predicts clinical outcome in multiple human cancers. Nat Genet, 38, 1043-8.
18. CHENG, X. H., BLACK, M., USTIYAN, V., LE, T., FULFORD, L., SRIDHARAN, A., MEDVEDOVIC, M., KALINICHENKO, V. V., WHITSETT, J. A. & KALIN, T. V. 2014. SPDEF inhibits prostate carcinogenesis by disrupting a positive feedback loop in regulation of the Foxm1 oncogene. PLoS Genet, 10, e1004656.

19. COSTA, R. H., KALINICHENKO, V. V., MAJOR, M. L. & RAYCHAUDHURI, P. 2005. New and unexpected: forkhead meets ARF. Curr Opin Genet Dev, 15, 42-48.

20. GORMALLY, M. V., DEXHEIMER, T. S., MARSICO, G., SANDERS, D. A., LOWE, C., MATAK-VINKOVIC, D., MICHAEL, S., JADHAV, A., RAI, G., MALONEY, D. J., SIMEONOV, A. & BALASUBRAMANIAN, S. 2014. Suppression of the FOXM1 transcriptional programme via novel small molecule inhibition. Nat Commun, 5, 5165 [Epub ahead of print].

21. GUSAROVA, G. A., WANG, I. C., MAJOR, M. L., KALINICHENKO, V. V., ACKERSON, T., PETROVIC, V. & COSTA, R. H. 2007. A cell-penetrating ARF peptide inhibitor of FoxM1 in mouse hepatocellular carcinoma treatment. J Clin Invest, 117, 99-111.

22. HALASI, M. & GARTEL, A. L. 2013. Targeting FOXM1 in cancer. Biochem Pharmacol, 85, 644-652.

23. KALIN, T. V., USTIYAN, V. & KALINICHENKO, V. V. 2011.

Multiple faces of FoxM1 transcription factor: Lessons from transgenic mouse models. Cell Cycle, 10, 396-405.

24. KALIN, T. V., WANG, I. C., ACKERSON, T. J., MAJOR, M. L., DETRISAC, C. J., KALINICHENKO, V. V., LYUBIMOV, A. & COSTA, R. H. 2006. Increased levels of the FoxM1 transcription factor accelerate development and progression of prostate carcinomas in both TRAMP and LADY transgenic mice. Cancer Res., 66, 1712-1720.

25. KALINICHENKO, V. V., MAJOR, M., WANG, X., PETROVIC, V., KUECHLE, J., YODER, H. M., SHIN, B., DATTA, A., RAYCHAUDHURI, P. & COSTA, R. H. 2004. Forkhead Box mlb Transcription Factor is Essential for Development of Hepatocellular Carcinomas and is Negatively Regulated by the p19ARF Tumor Suppressor. Genes & Development, 18, 830-850.

26. KORVER, W., ROOSE, J. & CLEVERS, H. 1997. The winged-helix transcription factor Trident is expressed in cycling cells. Nucleic Acids Res, 25, 1715-1719.

27. MCCORMICK, F. 1999. Signalling networks that cause cancer. Trends Cell Biol, 9, M53-M56.

28. MCGOVERN, U. B., FRANCIS, R. E., PECK, B., GUEST, S. K., WANG, J., MYATT, S. S., KROL, J., KWOK, J. M., POLYCHRONIS, A., COOMBES, R. C. & LAM, E. W. 2009. Gefitinib (Iressa) represses FOXM1 expression via FOXO3a in breast cancer. Mol Cancer Ther, 8, 582-91.

29. MIANNAY, B., MINVIELLE, S., ROUX, O., DROUIN, P., AVET-LOISEAU, H., GUERIN-CHARBONNEL, C., GOURAUD, W., ATTAL, M., FACON, T., MUNSHI, N. C., MOREAU, P., CAMPION, L., MAGRANGEAS, F. & GUZIOLOWSKI, C. 2017. Logic programming reveals alteration of key transcription factors in multiple myeloma. Sci Rep, 7, 9257.

30. MILEWSKI, D., PRADHAN, A., WANG, X., CAI, Y., LE, T., TURPIN, B., KALINICHENKO, V. V. & KALIN, T. V. 2017. FoxF1 and FoxF2 transcription factors synergistically promote rhabdomyosarcoma carcinogenesis by repressing transcription of p21Cip1 CDK inhibitor. Oncogene, 36, 850-862.

31. PILARSKY, C., WENZIG, M., SPECHT, T., SAEGER, H. D. & GRUTZMANN, R. 2004. Identification and validation of commonly overexpressed genes in solid tumors by comparison of microarray data. Neoplasia, 6, 744-750.

32. REN, X., SHAH, T. A., USTIYAN, V., ZHANG, Y., SHINN, J., CHEN, G., WHITSETT, J. A., KALIN, T. V. & KALINICHENKO, V. V. 2013. FOXM1 promotes allergen-induced goblet cell metaplasia and pulmonary inflammation. Mol Cell Biol, 33, 371-86.

33. SHERR, C. J. & MCCORMICK, F. 2002. The RB and p53 pathways in cancer. Cancer Cell, 2, 103-112.

34. SUN, L., REN, X., WANG, I. C., PRADHAN, A., ZHANG, Y., FLOOD, H. M., HAN, B., WHITSETT, J. A., KALIN, T. V. & KALINICHENKO, V. V. 2017. The FOXM1 inhibitor RCM-1 suppresses goblet cell metaplasia and prevents IL-13 and STAT6 signaling in allergen-exposed mice. Sci Signal, 10.

35. WANG, I. C., CHEN, Y. J., HUGHES, D., PETROVIC, V., MAJOR, M. L., PARK, H. J., TAN, Y., ACKERSON, T. & COSTA, R. H. 2005. Forkhead box M1 regulates the transcriptional network of genes essential for mitotic progression and genes encoding the SCF (Skp2-Cks1) ubiquitin ligase. Mol Cell Biol., 25, 10875-10894.

36. WANG, I. C., CHEN, Y. J., HUGHES, D. E., ACKERSON, T., MAJOR, M. L., KALINICHENKO, V. V., COSTA, R. H., RAYCHAUDHURI, P., TYNER, A. L. & LAU, L. F. 2008a. FoxM1 regulates transcription of JNK1 to promote the G1/S transition and tumor cell invasiveness. J Biol Chem, 283, 20770-8.

37. WANG, I. C., MELITON, L., TRETIAKOVA, M., COSTA, R. H., KALINICHENKO, V. V. & KALIN, T. V. 2008b. Transgenic expression of the forkhead box M1 transcription factor induces formation of lung tumors. Oncogene, 27, 4137-4149.

38. WANG, I. C., SNYDER, J., ZHANG, Y., LANDER, J., NAKAFUKU, Y., LIN, J., CHEN, G., KALIN, T. V., WHITSETT, J. A. & KALINICHENKO, V. V. 2012. Foxm1 mediates cross talk between Kras/mitogen-activated protein kinase and canonical Wnt pathways during development of respiratory epithelium. Mol Cell Biol, 32, 3838-50.

39. WANG, I. C., USTIYAN, V., ZHANG, Y., CAI, Y., KALIN, T. V. & KALINICHENKO, V. V. 2013. Foxm1 transcription factor is required for the initiation of lung tumorigenesis by oncogenic Kras. Oncogene.

40. YE, H., KELLY, T. F., SAMADANI, U., LIM, L., RUBIO, S., OVERDIER, D. G., ROEBUCK, K. A. & COSTA, R. H. 1997. Hepatocyte nuclear factor 3/fork head homolog 11 is expressed in proliferating epithelial and mesenchymal cells of embryonic and adult tissues. Mol Cell Biol, 17, 1626-1641.

41. ZHANG, N., WEI, P., GONG, A., CHIU, W. T., LEE, H. T., COLMAN, H., HUANG, H., XUE, J., LIU, M., WANG, Y., SAWAYA, R., XIE, K., YUNG, W. K., MEDEMA, R. H., HE, X. & HUANG, S. 2011. FoxM1 promotes beta-catenin nuclear localization and controls Wnt target-gene expression and glioma tumorigenesis. Cancer Cell, 20, 427-42.

What is claimed is:

1. A method of treating a proliferative disorder due to increased expression of the FOXM1 gene, comprising the step of administering a composition comprising

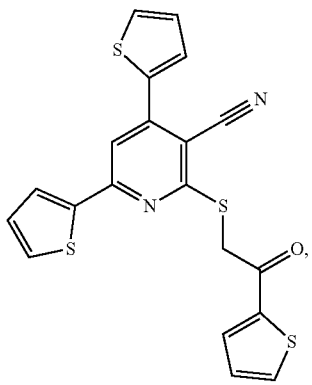

("RCM-1")

or a pharmaceutically acceptable salt thereof;
and a pharmaceutically acceptable excipient.

2. The method of claim 1, wherein said proliferative disorder is selected from a RASopathy, a LAM disease, a fibrotic disorder, a chronic inflammatory disorder, or a cancer.

3. The method of claim 1, wherein said proliferative disorder is cancer selected from an adenocarcinoma, a melanoma, a rhabdomyosarcoma, a non-small cell lung cancer (NSCLC), a head and neck squamous carcinoma, a hepatocellular carcinoma (HCC), an intrahepatic cholangiocarcinoma, a colon carcinoma, a basal cell carcinoma, an infiltrating ductal breast carcinoma, an anaplastic astrocytoma, a glioblastoma, a pancreatic carcinoma, a gastric cancer, an acute myeloid leukemia, a lung cancer, a liver cancer, a breast cancer, a prostate cancer, and a brain cancer.

4. The method of claim 1, wherein said proliferative disorder is selected from A549 lung adenocarcinoma and KPC-2 pancreatic carcinoma.

5. The method of claim 1, wherein said proliferative disorder or said cancer overexpresses FOXM1 and wherein said proliferative disorder or said cancer further contains a RAS mutation.

6. The method of claim 1, wherein said composition is administered in an amount sufficient to cause one or more of the following: a decrease in tumor growth, a decrease in tumor cell proliferation, increased tumor cell apoptosis, inhibition of metastatic dissemination of cancer, improvement in patient survival, reduced ability of tumor cells to form colonies, and reduced ability of tumor cells to migrate.

7. The method of claim 1, wherein said composition is administered to said individual in an amount sufficient to inhibit FOXM1 expression in cells overexpressing FOXM1 in said individual following administration of said composition to said individual.

8. A method of reducing the amount of a chemotherapeutic agent administered to an individual in need thereof, comprising the step of administering a composition of claim 1 to said individual prior to, concurrently with, or following administration of said chemotherapeutic agent.

9. The method of claim 8, wherein said chemotherapeutic agent is selected from a taxane, a platinum-based agent, an anthracycline, an alkylating agent, a *vinca* alkaloid, an epothilone, a histone deacetylase inhibitor, a topoisomerase I and II inhibitor, a kinase inhibitor, a nucleotide analog, a peptide antibiotic, and combinations thereof.

10. A composition comprising RCM-1, or a pharmaceutically acceptable salt thereof, and one or more chemotherapeutic agents selected from a taxane, a platinum-based agent, an anthracycline, an alkylating agent, a *vinca* alkaloid, an epothilone, a histone deacetylase inhibitor, a topoisomerase I and II inhibitor, a kinase inhibitor, a nucleotide analog, a peptide antibiotic, and combinations thereof.

11. The composition of claim 10, further comprising one or more chemotherapeutic agents selected from a taxane, a platinum-based agent, an anthracycline, an alkylating agent, a *vinca* alkaloid, an epothilone, a histone deacetylase inhibitor, a topoisomerase I and II inhibitor, a kinase inhibitor, a nucleotide analog, a peptide antibiotic, and combinations thereof.

* * * * *